United States Patent
Hsiao et al.

(10) Patent No.: US 12,292,445 B2
(45) Date of Patent: May 6, 2025

(54) METHODS OF SELECTING SUBJECTS FOR TREATMENT WITH METABOLOMIC MODULATORS

(71) Applicant: The Regents of the University of California, Oakland, CA (US)

(72) Inventors: Elaine Y. Hsiao, Los Angeles, CA (US); Jessica Yano, Los Angeles, CA (US); Helen E. Vuong, Los Angeles, CA (US); Christine Olson, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1203 days.

(21) Appl. No.: 17/057,500

(22) PCT Filed: May 22, 2019

(86) PCT No.: PCT/US2019/033435
§ 371 (c)(1),
(2) Date: Nov. 20, 2020

(87) PCT Pub. No.: WO2019/226723
PCT Pub. Date: Nov. 28, 2019

(65) Prior Publication Data
US 2021/0364526 A1  Nov. 25, 2021

Related U.S. Application Data

(60) Provisional application No. 62/675,743, filed on May 23, 2018.

(51) Int. Cl.
*G01N 33/68* (2006.01)
*A61K 35/74* (2015.01)
*A61P 25/08* (2006.01)
*G01N 33/94* (2006.01)

(52) U.S. Cl.
CPC ......... *G01N 33/6812* (2013.01); *A61K 35/74* (2013.01); *A61P 25/08* (2018.01); *G01N 33/9426* (2013.01); *G01N 2800/2857* (2013.01); *G01N 2800/52* (2013.01)

(58) Field of Classification Search
None
See application file for complete search history.

(56) References Cited

U.S. PATENT DOCUMENTS 11,116,804 B2 *  9/2021  Strandwitz .............. A61P 25/24

FOREIGN PATENT DOCUMENTS

WO  WO-2014075745 A1   5/2014
WO  WO-2019/226723 A1  11/2019

OTHER PUBLICATIONS

Pitkanen et al., "Advances in the development of biomarkers for epilepsy," The Lancet Neurology, 15(8): 843-856 (2016). (Year: 2016).*
Yunes, R.A. et al. GABA production and structure of gadB/gadC genes in Lactobacillus and Bifidobacterium strains from human microbiota. Anaerobe 42 (2016). pp. 197-204. (Year: 2016).*
International Search Report and Written Opinion for International Application No. PCT/US2019/033435 dated Aug. 29, 2019.
Olson et al., "The gut microbiota mediates the anti-seizure effects of the ketogenic diet," Cell, 173(7): 1728-1741 (2018).
Piccolo et al., "Plasma amino acid and metabolite signatures tracking diabetes progression in the UCD-T2DM rat model," American Journal of Physiology-Endocrinology and Metabolism, 310(11): E958-E969 (2016).
Pitkanen et al.. "Advances in the development of biomarkers for epilepsy," The Lancet Neurology, 15(8): 843-856 (2016).
Pollard et al., "The TARC/sICAM5 ratio in patient plasma is a candidate biomarker for drug resistant epilepsy," Frontiers in neurology, 3(181): 1-8 (2013).
Prugger et al., "Multiple biomarkers for the prediction of ischemic stroke: the PRIME study," Arteriosclerosis, thrombosis, and vascular biology, 33(3): 659-666 (2013).

* cited by examiner

*Primary Examiner* — Nghi V Nguyen
(74) *Attorney, Agent, or Firm* — Foley Hoag LLP; David P. Halstead; Allison L. Gilder

(57) ABSTRACT

Provided herein are methods for selecting a subject with a seizure disorder for treatment, as well as methods of treating the subject, determining the efficacy of the treatment, and adjusting the treatment dosage and frequency. In some aspects, provided herein are methods of treating seizures in a subject by administering to the subject a composition comprising bacteria of the *Akkermansia* (Akk) and *Parabacteroides* (Pb) genera.

20 Claims, 36 Drawing Sheets

METHODS OF SELECTING SUBJECTS FOR TREATMENT WITH METABOLOMIC MODULATORS

RELATED APPLICATIONS

This application is a § 371 national-stage application based on PCT/US19/33435, filed May 22, 2019, which claims a right of priority from and the benefit of an earlier filing date of U.S. Provisional Application No. 62/675,743, filed May 23, 2018, which is hereby incorporated by reference herein in its entirety.

BACKGROUND

The ketogenic diet (KD) is an effective treatment for refractory epilepsy, a condition affecting more than one-third of epileptic individuals and defined by a failure to respond to existing anticonvulsant medications, but the specific mechanisms underlying its neuroprotective effects remain unclear. Despite its value for treating epilepsy and its increasing application to disorders, including autism spectrum disorder, Alzheimer's disease, metabolic syndrome and cancer, use of the KD remains low due to difficulties with implementation, dietary compliance and adverse side effects. Novel molecular targets are needed to develop viable clinical interventions for intractable epilepsy and other disorders for which the KD is beneficial. Many studies have proposed roles for ketone bodies, gamma-aminobutyric acid (GABA) modulation, and mitochondrial anaplerosis in mediating the neurological effects of the KD, but exactly how the KD alters brain activity and behavior remains unclear.

The gut microbiota is a key intermediary between diet and host physiology; the species composition and function of the gut microbiota is critically shaped by diet, and many nutrients made available to the host depend on microbial metabolism. Diet-induced changes in the gut microbiota are reproducible and persistent, and as such, have lasting impact on the host. Several diet-induced host pathologies are mediated by changes in the gut microbiota in mouse models, including symptoms of atherosclerosis in response to the carnitine-rich diet, undernutrition in response to the Malawian diet and abnormal social behavior in response to maternal high-fat diet.

Increasing evidence reveals that the microbiota influences the development and function of the nervous system. The microbiota affects many factors relevant to neurotransmission, including neurotransmitter signaling, synaptic protein expression, long-term potentiation, and myelination. Several clinical studies link antibiotic treatment to increased risk of status epilepticus or symptomatic seizures in epileptic individuals, suggesting a possible role for the microbiota in mitigating seizure likelihood.

SUMMARY

Methods for selecting a subject for treatment with a composition that mimics the effects of a ketogenic diet, as well as methods of treating the subject, determining the response to treatment, and adjusting the treatment dosage and frequency are provided.

In some aspects, methods of selecting a subject afflicted with a seizure disorder are disclosed. Such methods include (a) detecting, in a biological sample from a subject, presence, absence, amount, or activity of at least one biomarker associated with a seizure disorder; (b) comparing the presence, absence, amount, or activity of the at least one biomarker in (a) to presence, absence, amount, or activity of the same biomarker in a reference sample representative of a subject without the seizure disorder; and (c) selecting the subject when the presence, absence, amount, or activity of the at least one biomarker in the biological sample from the subject differs from the presence, absence, amount, or activity of the same biomarker in the reference sample. In some embodiments of these methods, the biological sample is a fecal sample or a serum sample.

In an aspect, methods of treating a subject afflicted with a seizure disorder are disclosed. These methods include (a) selecting a subject afflicted with a seizure disorder in whom presence, absence, amount, or activity of at least one biomarker associated with a seizure disorder differs from presence, absence, amount, or activity of the same biomarker in a reference sample representative of a subject without the seizure disorder; and (b) administering to the subject afflicted with the seizure disorder an effective amount of a pharmaceutical composition to treat the seizure disorder. In some embodiments, the pharmaceutical composition comprises bacteria of the *Akkermansia* (Akk) and *Parabacteroides* (Pb) genera. In some aspects, such pharmaceutical compositions for use in treating a subject afflicted with a seizure disorder or for use in manufacturing/preparing a formulation/medicament to treat a subject afflicted with a seizure disorder are provided.

In any of the disclosed aspects, the biomarker associated with a seizure disorder can be any one or more of the biomarkers disclosed in FIGS. 6 through 17. The seizure disorder can be refractory epilepsy, non-refractory epilepsy, autism spectrum disorder, Rett syndrome, fragile X, attention deficit disorder (ADD), or attention-deficit/hyperactivity disorder (ADHD). The presence, absence, amount, or activity of the at least one biomarker in the biological sample from the subject differs from the presence, absence, amount, or activity of the same biomarker in the reference sample in some embodiments in that (a) the biomarker is present in the biological sample but absent in the reference sample; (b) the biomarker is absent in the biological sample but present in the reference sample; (c) the amount or activity of the biomarker is at least 20% higher in the biological sample as compared to its amount or activity, respectively, in the reference sample; or (d) the amount or activity of the biomarker is at least 20% lower in the biological sample as compared to its amount or activity, respectively, in the reference sample.

Methods for selecting and treating a subject typically include: (a) obtaining a biological sample from the subject; (b) measuring the presence, absence, amount, or activity of at least one biomarker associated with a disorder; (c) comparing the presence, absence, amount, or activity of the at least one biomarker in (b) to the presence, absence, amount or activity of the same biomarker in a reference sample representative of a subject without the disorder; (d) selecting the subject for treatment if the subject meets criteria comprising: the absence, amount, or activity of the at least one biomarker in the biological sample is (or in some aspects, differs by) at least 20%, 25%, 30%, 35%, 40%, 50%, 55%, 60%, 65%, 70%, 75%, 80%, 85%, 90%, 100%, or more than 100% relative to the biomarker in the reference sample; and (e) optionally administering to the subject an effective amount of a composition comprising bacteria of the *Akkermansia* (Akk) and *Parabacteroides* (Pb) genera to treat the disorder.

Methods for determining the responsiveness of a subject to therapy comprising a composition comprising bacteria of the *Akkermansia* (Akk) and *Parabacteroides* (Pb) genera typically include: (a) obtaining a first biological sample from the subject; (b) measuring the presence, absence, amount, or activity of at least one biomarker associated with a disorder; (c) administering a therapeutically effective amount of the composition to the subject; (d) obtaining a second biological sample from the subject; and (e) measuring the presence, absence, amount, or activity of the at least one biomarker in the second biological sample; wherein the subject is responsive to therapy if the presence, absence, amount, or activity of the at least one biomarker in the second biological sample is at least 20%, 25%, 30%, 35%, 40%, 50%, 55%, 60%, 65%, 70%, 75%, 80%, 85%, 90%, 100%, or less than 100% relative to the biomarker in the first biological sample and the methods further comprise administering one or more additional treatments of the composition.

In certain embodiments, methods for determining the responsiveness of a subject to therapy comprising administration of a composition comprising bacteria of the *Akkermansia* (Akk) and *Parabacteroides* (Pb) genera can also include: (a) obtaining a first biological sample from the subject; (b) measuring the presence, absence, amount, or activity of at least one biomarker associated with a disorder in the first biological sample; (c) administering a therapeutically effective amount of the composition to the subject; (d) obtaining a second biological sample from the subject; and (e) measuring the presence, absence, amount, or activity of the at least one biomarker in the second biological sample; wherein the subject is determined to be responsive to the therapy if the presence, absence, amount, or activity of the at least one biomarker in the first biological sample differs by at least 20%, 25%, 30%, 35%, 40%, 50%, 55%, 60%, 65%, 70%, 75%, 80%, 85%, 90%, 100%, or more than 100% relative to the biomarker in the second biological sample. The methods may further comprise administering one or more additional treatments of the composition if the subject is responsive to therapy.

Methods for adjusting the dosage of a composition comprising bacteria of the *Akkermansia* (Akk) and *Parabacteroides* (Pb) genera typically include: (a) administering a therapeutically effective amount of the composition to a subject afflicted with a disorder; (b) obtaining a biological sample from the subject; (c) measuring the presence, absence, amount, or activity of at least one biomarker in the biological sample; (d) comparing the presence, absence, amount, or activity of the biomarker in (c) to the presence, absence, amount, or activity of the same biomarker in a reference sample representative of a subject without the disorder; and (e) increasing the dosage of the composition if the presence, absence, amount, or activity of the biomarker in the biological sample is (or in some aspects, differs by) at least 20%, 25%, 30%, 35%, 40%, 50%, 55%, 60%, 65%, 70%, 75%, 80%, 85%, 90%, 100%, or greater than 100% relative to the biomarker in the reference sample. The dosage of the composition is decreased if the presence, absence, amount, or activity of the biomarker in the biological sample is at least 20%, 25%, 30%, 35%, 40%, 50%, 55%, 60%, 65%, 70%, 75%, 80%, or less than 80% relative to the biomarker in the reference sample. In some embodiments, the dosage of the composition is decreased if the presence, absence, amount, or activity of the biomarker in the biological sample differs by less than 20% relative to the biomarker in the reference sample.

In some embodiments, the biomarker(s) is a biochemical(s) associated with lipid metabolism, carbohydrate metabolism, or amino acid metabolism. The method may also include detecting the level of one or more biomarkers such as GABA/glutamate ratios and/or glutamine levels (e.g., in the brain, in the hippocampus), and combinations thereof. In some embodiments, the levels of 5, 10, 20, 25, or more biomarkers are determined.

In some embodiments, the biomarker is a serum ketogenic amino acid (e.g., leucine, lysine, threonine, tryptophan, tyrosine). In some embodiments, the biomarker is a gamma-glutamyl amino acid (e.g., gamma-glutamyl (GG)-leucine, gamma-glutamyl (GG)-lysine, gamma-glutamyl (GG)-threonine, gamma-glutamyl (GG)-tryptophan, gamma-glutamyl (GG)-tyrosine).

In some embodiments, the biomarker is arabonate/xylonate, N-acetylmethionine, myristoleoylcarnitine (C14:1), cytidine 5'-monophosphate (5'-CMP), 1-palmitoyl-2-linoleoyl-digalactosylglycerol (16:0/18:2), riboflavin (Vitamin B2), ursocholate, isovalerate, glucoronate, creatinine, 1-palmitoyl-GPI (16:0), pipecolate, campesterol, laurylcarnitine (C12), glucose, ethylmalonate, delta-tocopherol, palmitoylcarnitine (C16), picolinate, 6-oxolithocholate, cysteine, 2-oxoarginine, N6-formyllysine, ribulose/xylulose, 3-ureidopropionate, 3-methylcytidine, N6-carboxymethyllysine, N-formylphenylalanine, 3-methyl-2-oxobutyrate, 4-guanidinobutanoate, p-cresol sulfate, imidazole propionate, phenylacetylglycine, perfluorooctanesulfonic acid (PFOS), ergothioneine, indolepropionate, tauro-beta-muricholate, p-cresol-glucuronide, cholate, indoleacrylate, 1-palmitoleoylglycerol (16:1), cystathionine, 3-methylglutaconate, palmitoleate (16:1n7), sphingomyelin (d18:1/25:0 d19:0/24:1d20:1/23:0d19:1/24:0), decanoylcarnitine (C10), 17-methyl stearate, 1-palmitoleoyl-GPC (16:1), stearoyl sphingomyelin (d18:1/18:0), 4-hydroxyhippurate, N6-carboxymethyllysine, valylleucine, 1-palmitoyl-2-oleoyl-GPI (16:0/18:1), lysine, urea, valerylcarnitine (C5), betaine, indoleacetylglycine, or tyrosine. In other embodiments, the biomarker is octanoylcarnitine (C8), 1-methylnicotinamide, ursodeoxycholate, gamma-glutamyl-epsilon-lysine, 7-ketodeoxycholate, 3-(4-hydroxyphenyl)propionate, 1-palmitoyl-2-oleoyl-GPG (16:0/18:1), dihydrobiopterin, glycerophosphoglycerol, linoleoylcarnitine (C 18:2), palmitoylcholine, 1-stearoyl-GPC (18:0), 2-hydroxyglutarate, indoleacetate, 3-sulfo-L-alanine, glutarate (pentanedioate), p-aminobenzoate (PABA), maltose, stearoylcholine, erythronate, maltotriose, spermine, gamma-glutamyltyrosine, N-formylmethionine, mevalonate, gamma-glutamylhistidine, 3-sulfo-L-alanine, mannitol/sorbitol, gamma-glutamyltryptophan, 1-methylguanidine, homostachydrine, palmitoyl dihydrosphingomyelin, N-trimethyl 5-aminovalerate, sphingomyelin (d18:0/18:0 d19:0/17:0), homoarginine, pyridoxate, behenoyl dihydrosphingomyelin (d18:0/22:0), 10-undecenoate (11:1n1), sphingomyelin (d18:1/19:0 d19:1/18:0), sphingomyelin (d18:1/18:1 d18:2/18:0), choline, 2-palmitoleoyl-GPC (16:1), dihomo-linoleoylcarnitine (C20:2), glycosyl-N-stearoyl-sphingosine, palmitoyl dihydrosphingomyelin (d18:0/16:0), stearoylcarnitine (C18), 1-stearoyl-2-linoleoyl-GPC (18:0/18:2), 1-palmitoyl-2-linoleoyl-GPI (16:0/18:2), 2,3-dihydroxy-2-methylbutyrate, 3-methyl-2-oxobutyrate, N-behenoyl-sphingadienine (d18:2/22:0), pyroglutamine, taurocyamine, phenol sulfate, 1-stearoyl-2-oleoyl-GPC (18:0/18:1), dihomo-linolenoylcarnitine, or xanthurenate. In certain embodiments, the amounts of arabonate/xylonate, N-acetylmethionine, myristoleoylcarnitine (C14:1), riboflavin (Vitamin B2), glucoronate, creatinine, octanoylcarnitine, 1-methylnicotinamide, gamma-glutamyl-epsilon-lysine, dihydrobiopterin, urea, taurocholenate sulfate, laurylcarnitine (C12), creatine, bilirubin (Z Z), and myristoylcarnitine (C14) are increased in the subject. In some embodiments, an amount of at least one of these biomarkers is increased in the subject.

In other embodiments, the amounts of 1-palmitoyl-GPI (16:0), campesterol, laurylcarnitine (C12), delta-tocopherol, palmitoylcarnitine (C16), linoleoylcarnitine (C18:2), palmitoylcholine, 1-stearoyl-GPC (18:0), stearoylcholine, diglycerol, stimasterol, 2-stearoylcholine, stigmasterol, 2-stearoyl-GPE (18:0), myristoylcarnitine (C14), oleoylcarnitine (C18:1) and stearoylcarnitine are increased in the subject. In some embodiments, an amount of at least one of these biomarkers is increased in the subject. In yet other embodiments, the amounts of 3-ureidopropionate, 3-methylcytidine, mevalonate, diglycerol, and lignoceroylcarnitine (C24) are increased in the subject. In some embodiments, an amount of at least one of these biomarkers is increased in the subject. In other embodiments, the amount of PFOS, ergothionneinem tauro-bea-muricholate, 1-methylguanidine homostachydrine, palymitoyl dihydrosphingomyelin, sphingomyelin, pyridoxate, riboflavin (Vitamin B2), behenoyl dihydrosphingomyelin (d18:0/22:0), 10-undecenoate (11:1n1), tartrate, sphingomyelin (d18:0/20:0 d16:0/22:0), N-stearolytaurine, sphingomyelin (d18:1/17:0 d17:1/18:0 d19:1/16:0), O-sulfo-L-tyrosine, sphingomyelin (d18/1/19:0 d19:1/8:0, cysteine s-sulfate, and sphingomyelin (d18:2/18:1) are increased in the subject. In some embodiments, an amount of at least one of these biomarkers is increased in the subject.

In other embodiments, the amounts of 3-methylglutaconate, ribulose/xylulose, decanoylcarnitine (C10), stearoyl sphingomyelin (d18:1/18:0), betaine, sphingomyelin (d18:1/19:0 d18:1/18:0), sphingomyelin (d18:1/18:1 d18:2/18:0), choline, dihomo-linoleoylcarnitine (C20:2), gylosyl-N-stearoyl-sphingosine, palmitoyl dihydrosphingomyelin (d18:0/16:0), stearoylcarnitine (C18), 1-stearoyl-2-linoleoyl-GPC (18:0/18:2), N-acetyl-1-methylhistidine, palmitoyl sphingomyelin (d18:1/16:0), sphingomyelin (d18:2/24:2), cis-4-decenoylcarnitine (C10:1), oleoylcarnitine (C18:1), 3 4-methylene heptanoylglycine, and sphingomyelin (d18:2/18:1) are increased in the subject. In some embodiments, an amount of at least one of these biomarkers is increased in the subject. In yet other embodiments, the amount of valerylcarnitine (C5), betaine, pyroglutamine, taurocyamine, phenol sulfate, dihomo-linolenoylcarnitine, and N-octanoylglycine is increased in the subject. In some embodiments, an amount of at least one of these biomarkers is increased in the subject.

In other embodiments, the amount of cytidine 5'-monophosphate (5'-CMP), 1-palmitoyl-2-linoleoyl-digalactosylglycerol (16:0/18:2), ursocholate, isovalerate, pipecolate, glucose, ethylmalonate, picolinate, 6-oxolithocholate, cysteine, 2-oxoarginine, N6-formyllysine, p-cresol sulfate, imidazole propionate, phenylacetylglycine, 1-palmitoleoylglycerol (16:1), cystathionine, palmitoleate (16:1n7), 4-hydroxyhippurate, 1-palmitoyl-2-oleoyl-GPI (16:0/18:1), and valylleucine is decreased in the subject. In some embodiments, an amount of at least one of these biomarkers is decreased in the subject.

In some embodiments of the methods disclosed herein, a metric (e.g., amount, activity, level of presence) of a biomarker listed with an asterisk in FIG. 6 or 9, or without an asterisk in FIG. 7, 8, 10, or 11 differs by being lower in the reference sample representative of a subject without the disorder than in the biological sample from the subject afflicted with the disorder or by being higher in the first biological sample from a subject afflicted with the disorder than in the second biological sample from the subject after the administration of a therapeutically effective amount of the composition. In some embodiments of the methods disclosed herein, a metric (e.g., amount, activity, level of presence) of a biomarker listed without an asterisk in FIG. 6 or 9, or with an asterisk in FIG. 7, 8, 10, or 11 differs by being higher in the reference sample representative of a subject without the disorder than in the biological sample from the subject afflicted with the disorder or by being lower in the first biological sample from a subject afflicted with the disorder than in the second biological sample from the subject after the administration of a therapeutically effective amount of the composition.

In various embodiments, additional biomarkers or combinations of biomarkers can be used by relying on the information provided in FIGS. 6 through 17.

Preferred probiotic compositions for treating the subject are also provided and include, for example, compositions comprising bacteria of Akkermansia genus (Akk) (e.g., Akkermansia muciniphila) and Parabacteroides genus (Pb) (e.g., Parabacteroides merdae or Parabacteroides distasonis). Either Akk or Pb (or the two considered together) can be present at an amount greater than 10%, 20%, 30%, 40%, 50%, 60%, 70%, 80%, or 90% of the bacteria in the composition. The methods can be used to modulate the metabolism of biochemicals associated with lipid metabolism, carbohydrate metabolism, and amino acid metabolism in the subject. For example, if the disease or disorder is characterized by increased ketogenic gamma-glutamylated amino acids, the probiotic composition can be one that modulates gamma-glutamylation itself or selective metabolism of ketogenic gamma-glutamylated amino acids, or a combination thereof.

In the disclosed methods, the subject can be a human. In some embodiments, the compositions and methods are utilized to treat and prevent seizures in a subject (e.g., a subject with a neurodevelopmental disorder, such as an autism spectrum disorder, Rett syndrome, fragile X, attention deficit disorder (ADD), attention-deficit/hyperactivity disorder (ADHD), refractory epilepsy, and/or non-refractory epilepsy). In some embodiments, the neurodevelopmental condition can be Alzheimer's disease, Huntington's disease, Parkinson's disease, amyotrophic lateral sclerosis (ALS), cancer, stroke, a metabolic disease, a mitochondrial disorder, depression, migraines, or traumatic brain injury (TBI).

In some embodiments, the biological sample is serum. In other embodiments, the biological sample is feces.

BRIEF DESCRIPTION OF THE FIGURES

FIG. 1A shows 6-Hz seizure thresholds in response to oral gavage with the GGT inhibitor, GGsTop, in SPF mice fed CD (left). n=6, 9. Behavior in seizure-tested mice (right). Line at y=10 seconds represents threshold for scoring seizures, and yellow triangle at 24 mA denotes starting current per experimental cohort. n=16. FIG. 1B shows 6-Hz seizure thresholds in response to supplementation with ketogenic amino acids in Abx-treated SPF mice enriched for *A. muciniphila* and *Parabacteroides* spp (left). n=5, 6. Behavior in seizure-tested mice (right). Yellow line at y=10 seconds represents threshold for scoring seizures, and yellow triangle at 24 mA denotes starting current per experimental cohort. n=12. FIG. 1C shows total GGT activity per 100 mg feces from SPF CD, SPF KD, AkkPb KD, or AkkPb CD mice (left), and inhibition by GGsTop (right). n=5. FIG. 1D shows total GGT activity per 100 mg feces from SPF CD animals treated with vehicle, *A. muciniphila* and *Parabacteroides* spp. probiotic, or heat-killed bacteria for bi-daily for 28 days (left), and inhibition by GGsTop (right). n=5. Data are presented as mean±s.e.m. Student's t-test (1A, 1B), Two-way ANOVA with Bonferroni (1C, 1D). SPF=specific pathogen-free (conventionally-colonized), CD=control diet, KD=ketogenic diet, CC50=current intensity producing seizures in 50% of mice tested, AA=amino acids, veh=vehicle, Abx=pre-treated with antibiotics (ampicillin, vancomycin, neomycin, metronidazole [AVNM]), AkkPb=*A. muciniphila, P. merdae* and *P. distasonis*, GGsTop=GGT inhibitor, PbM=*Parabacteroides merdae*, Akk=*Akkermansia muciniphila*, M9=minimal media, GGT=gamma-glutamyltranspeptidase, AU=absorbance units.

Figure 2:
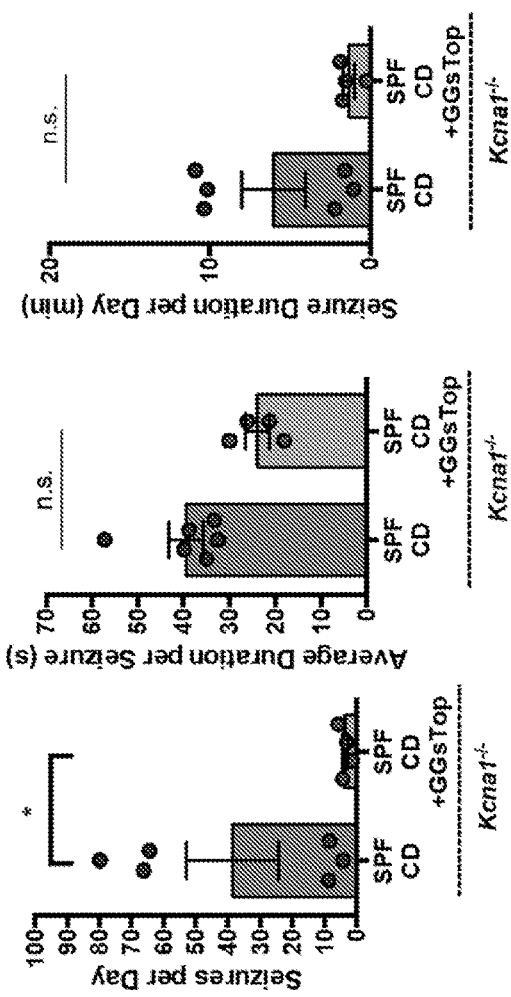
Figure 2:
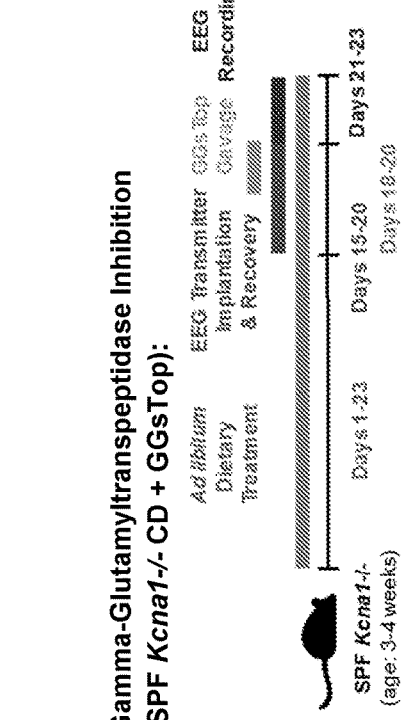

FIG. 2 shows a schematic of the gamma-glutamyltranspeptidase inhibition experiment and average number of seizures per day (left), average duration per seizure (middle) and total duration of seizures per day (right) in SPF CD Kcna1−/− mice treated with GGsTop. Data are presented as non-parametric Kolgomorov-Smirnov t test. SPF=specific pathogen-free (conventionally-colonized), CD=control diet, KD=ketogenic diet, veh=vehicle, Abx=pre-treated with antibiotics (ampicillin, vancomycin, neomycin, metronidazole [AVNM]), AkkPb=*A. muciniphila, P. merdae* and *P. distasonis*.

Figure 3A:
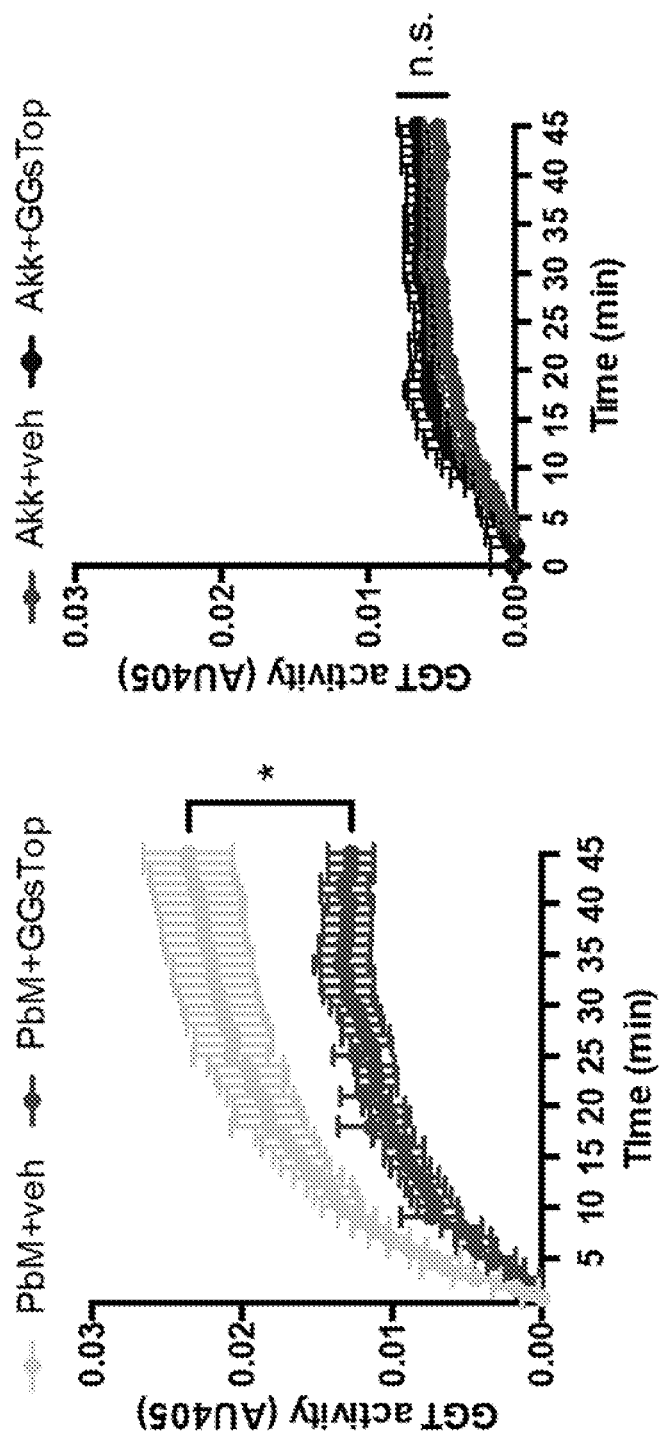
Figure 3B:
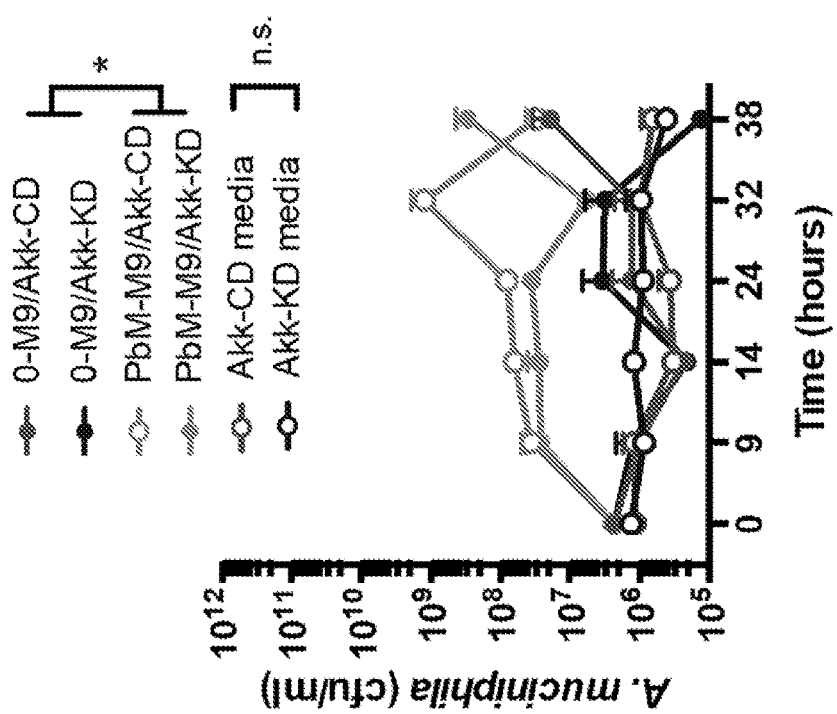
Figure 3C:
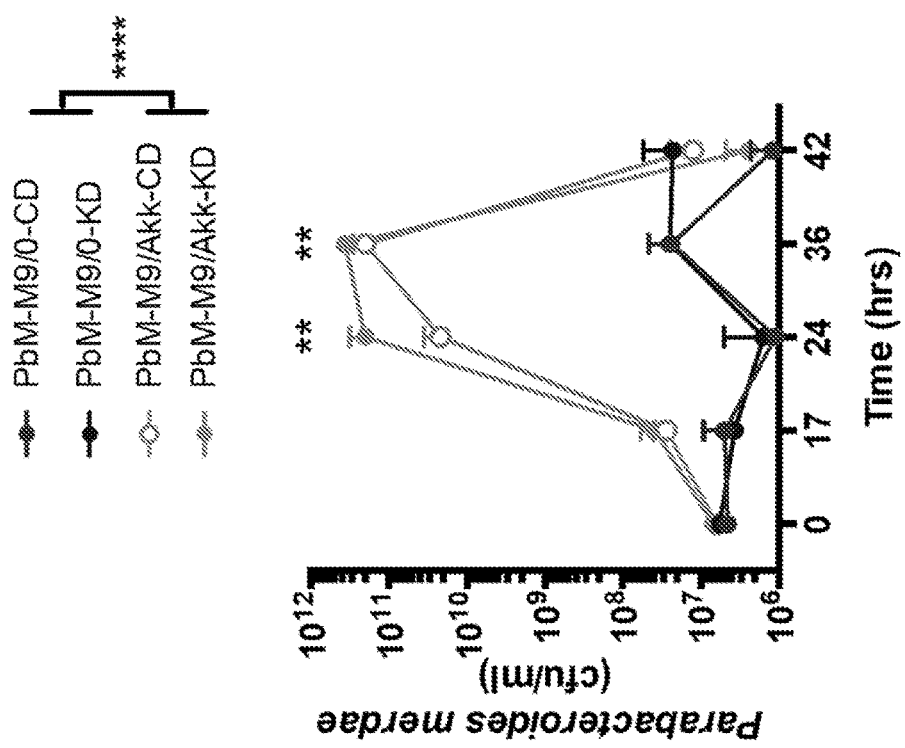
Figure 3D:
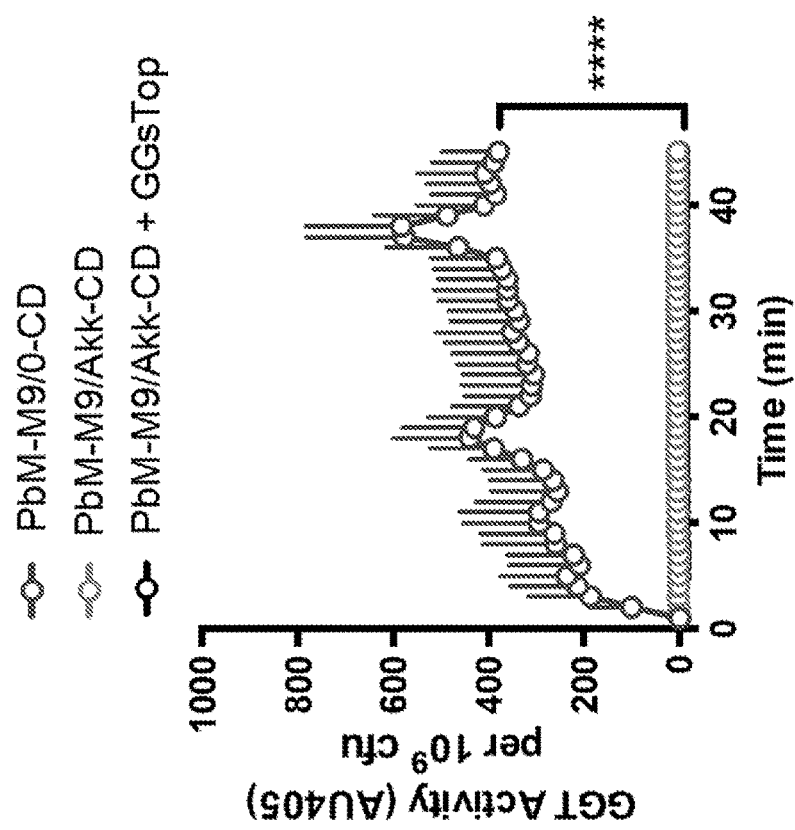
Figure 3E:
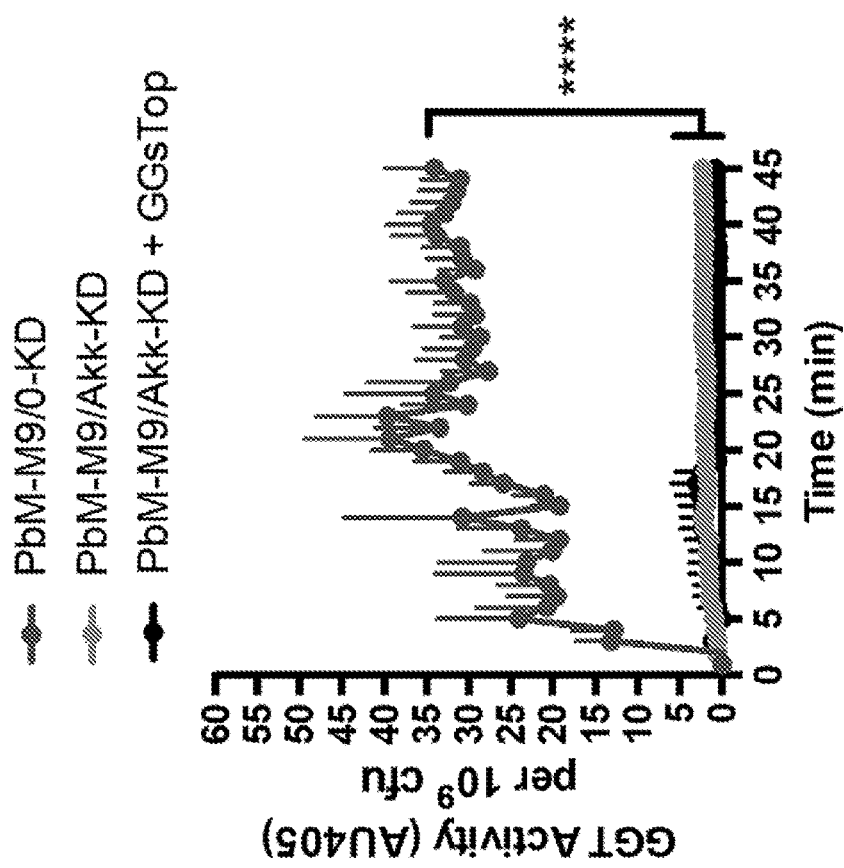

FIGS. 3A through 3E show amino acid effects on seizures, bacterial GGT activity and dietary modulation of bacterial genes for amino acid metabolism. FIG. 3A shows GGT activity in conventionally-cultured *Parabacteroides merdae* (left) and *A. muciniphila* (right), treated with GGsTop or vehicle. n=5. FIG. 3B shows (left) levels of live *A. muciniphila* (Akk) after incubation in CD vs. KD culture media or in CD or KD agar overlaid with M9 minimal media containing live *Parabacteroides merdae* (PbM) or no bacteria (0). n=3. FIG. 3C shows levels of live PbM after incubation in M9 minimal media overlaid on CD or KD agar containing Akk or no bacteria (0). n=5. FIG. 3D shows GGT activity in *P. merdae* grown in M9 media overlaid on CD agar containing *A. muciniphila* or no bacteria at t=24 hrs, and inhibition of GGT activity by GGsTop. n=5. FIG. 3E shows GGT activity in *P. merdae* grown in M9 media overlaid on KD agar containing *A. muciniphila* or no bacteria at t=24 hrs, and inhibition of GGT activity by GGsTop. n=5.

Figure 4:
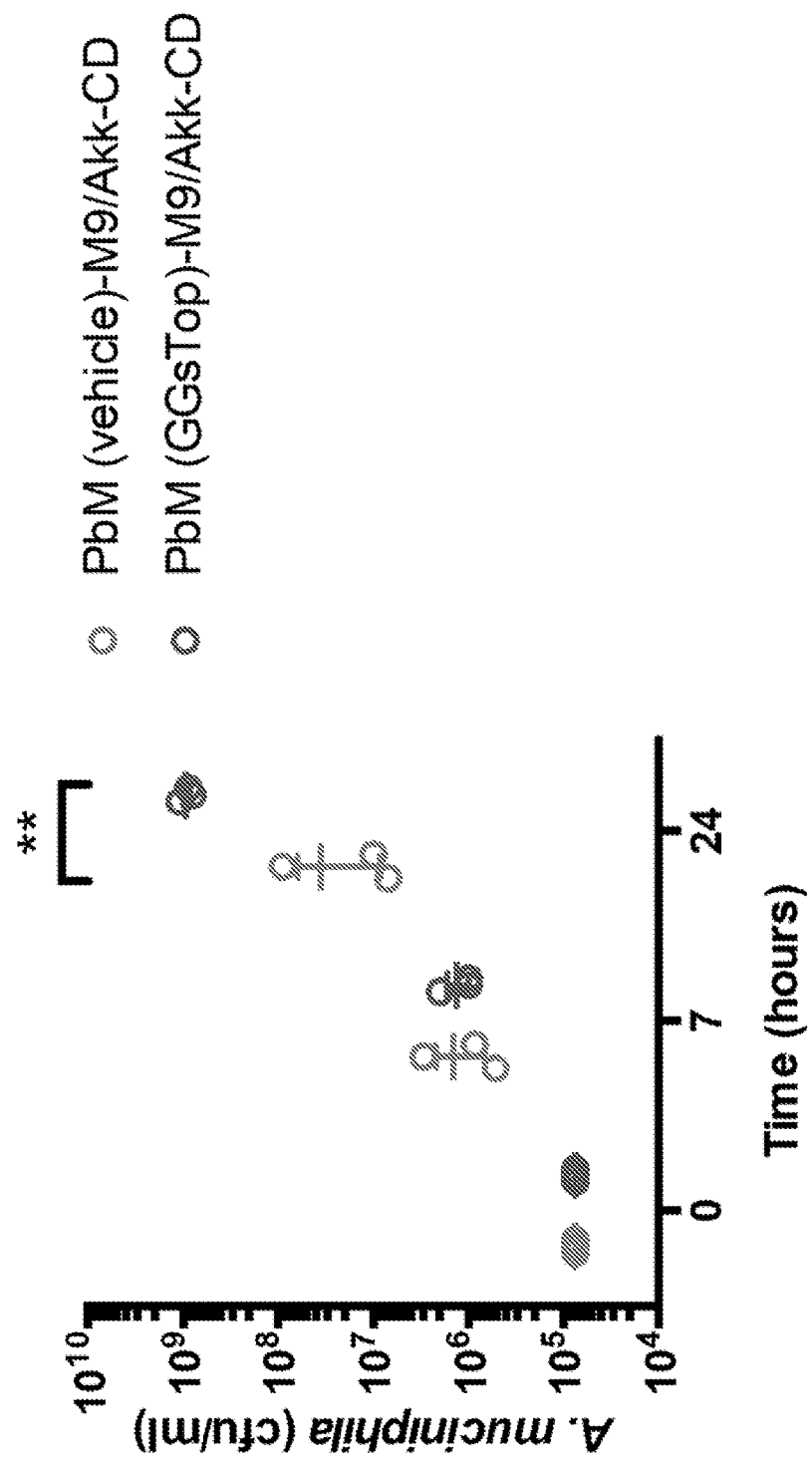

FIG. 4 shows the levels of *A. muciniphila* (Akk) after 0, 7, or 24 hours incubation in CD agar overlaid with *P. merdae* (PbM) that was pre-treated with vehicle or GGsTop in M9 minimal media. n=3. Data are presented as Two-way ANOVA with Bonferroni (b): **P<0.01, PbM=*Parabacteroides merdae*, Akk=*Akkermansia muciniphila*, GGsTop=GGT inhibitor, GGT=gamma-glutamyltranspeptidase, AU=absorbance units.

Figure 5:
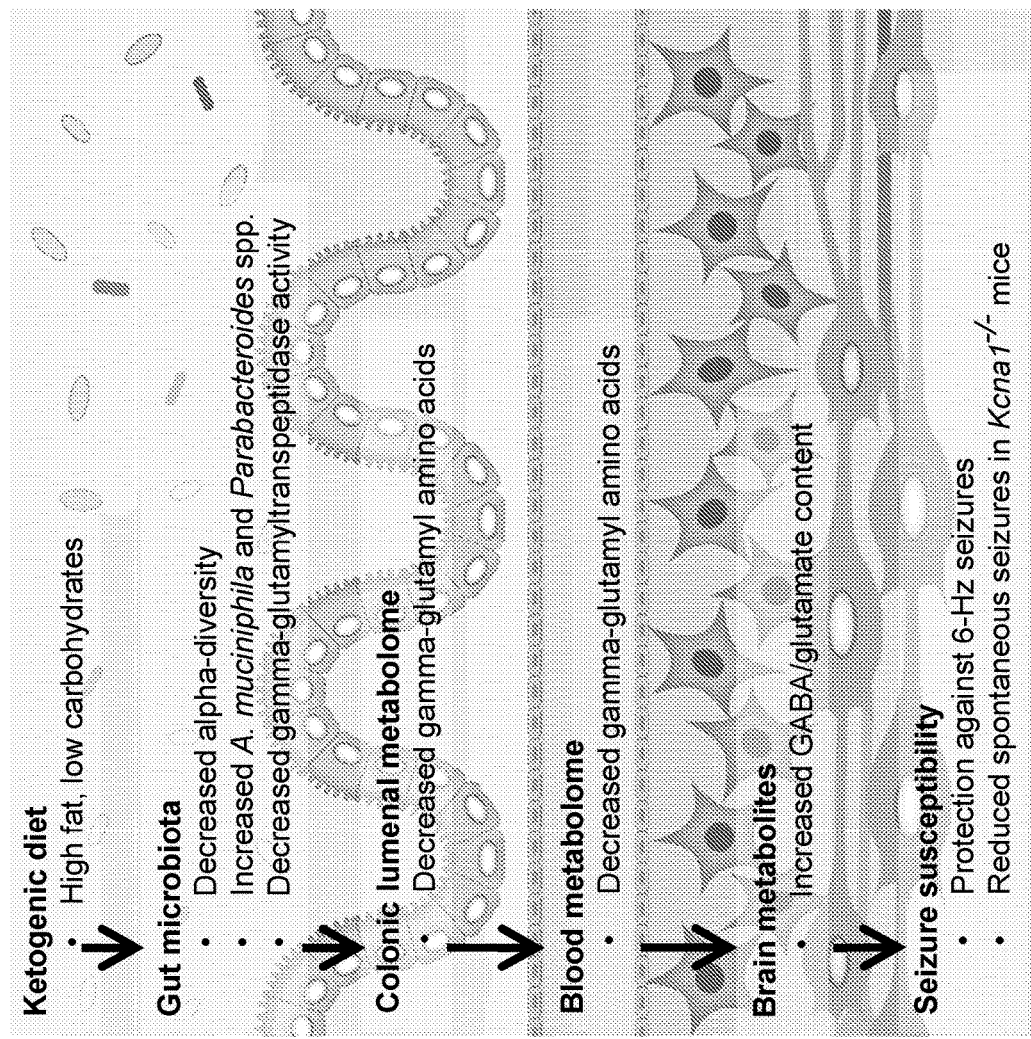

FIG. 5 shows a model for the effects of the KD on the gut microbiome and seizure protection. The high fat, low carbohydrate KD decreases alpha-diversity of the gut microbiota, while enriching relative abundance of particular bacterial taxa that can subsist in polysaccharide-restricted environments, including *A. muciniphila* and *Parabacteroides* spp. The KD and cross-feeding between bacteria, including *A. muciniphila* and *Parabacteroides* spp., decreases gamma-glutamyltranspeptidase activity of the gut microbiota. As a result, decreased levels of gamma-glutamyl amino acids are detected in the colonic lumen and the blood, among many other microbiota-related metabolomic alterations. Gamma-glutamyl amino acids exhibit altered transport properties, where the brain relies on peripheral amino acid transport for regulation of central metabolism of neurochemicals, including GABA and glutamate. The KD microbiota, and *A. muciniphila* and *Parabacteroides* spp. in particular, sufficiently raise hippocampal GABA/glutamate ratios and protect against induced 6-Hz psychomotor seizures in wild-type mice as well as spontaneous tonic-clonic seizures in Kcna1 deficient mice.

Figure 6:
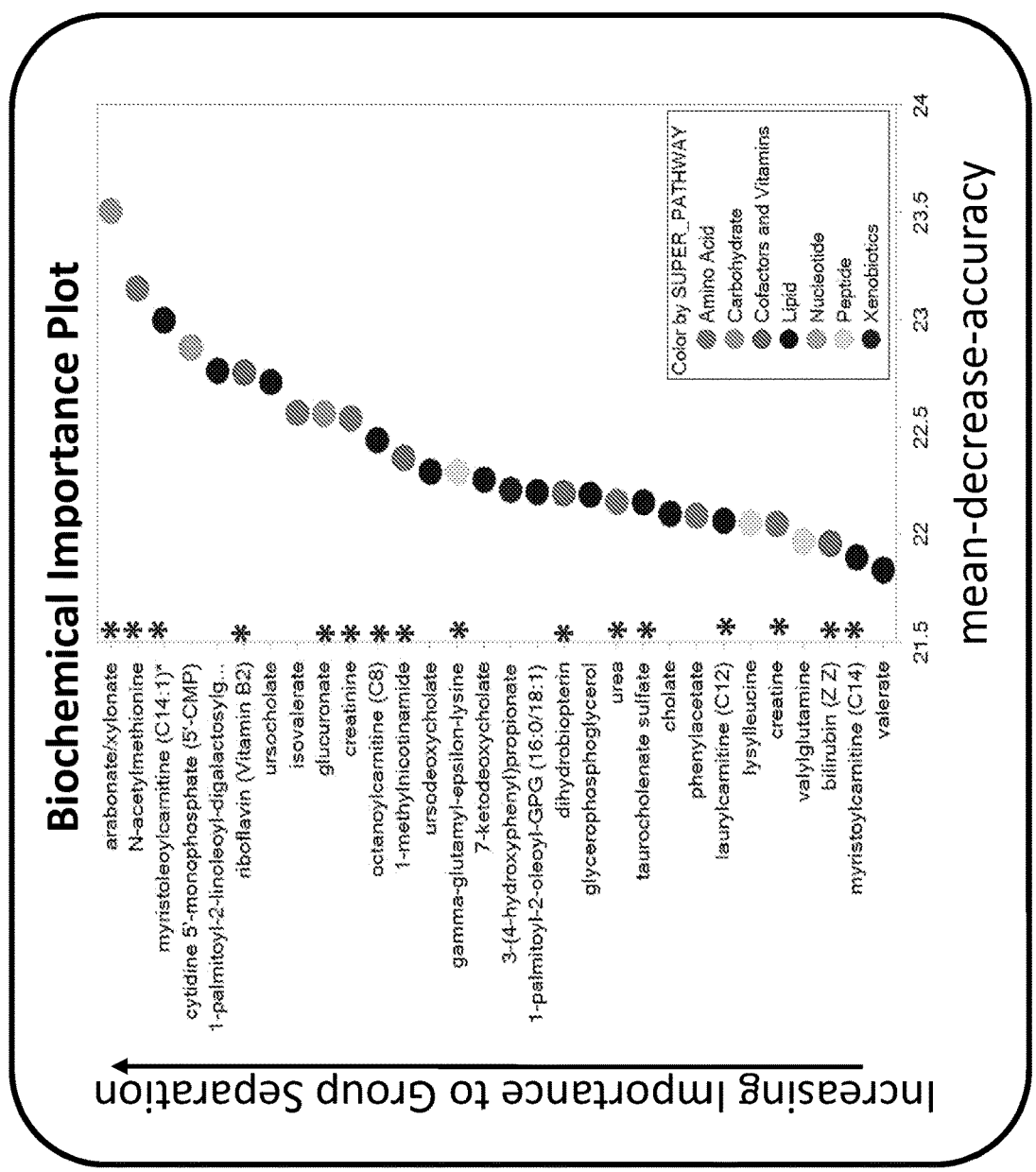

FIG. 6 shows a table of Random Forest classification of most discriminatory metabolites in fecal samples from groups treated with and without antibiotics. * denotes biomarkers that are elevated. Biomarkers without * were reduced.

Figure 7:
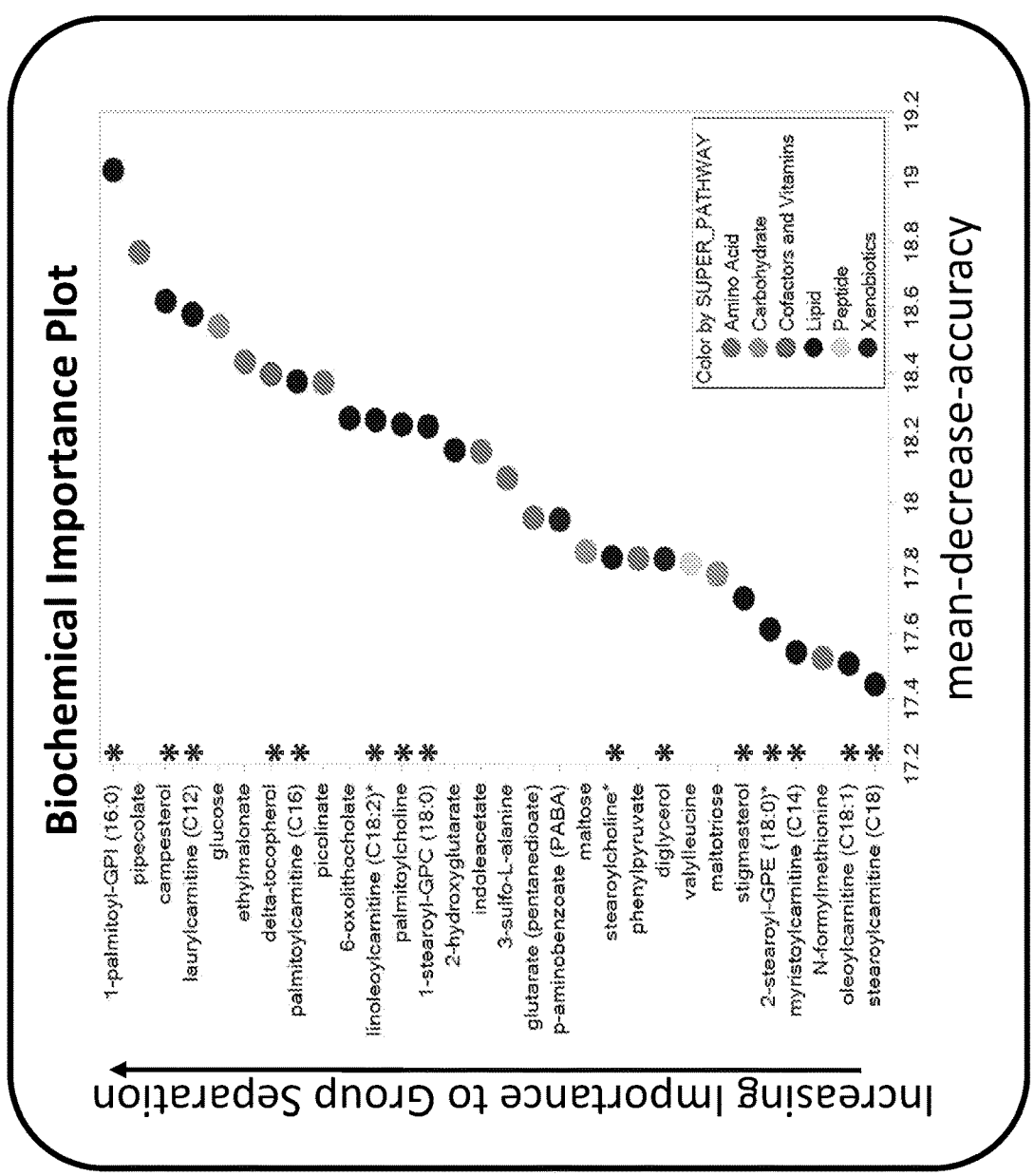

FIG. 7 shows a table of Random Forest classification of most discriminatory metabolites in fecal samples from mice fed a control diet versus mice fed a ketogenic diet. * denotes biomarkers that are elevated. Biomarkers without * were reduced.

Figure 8:
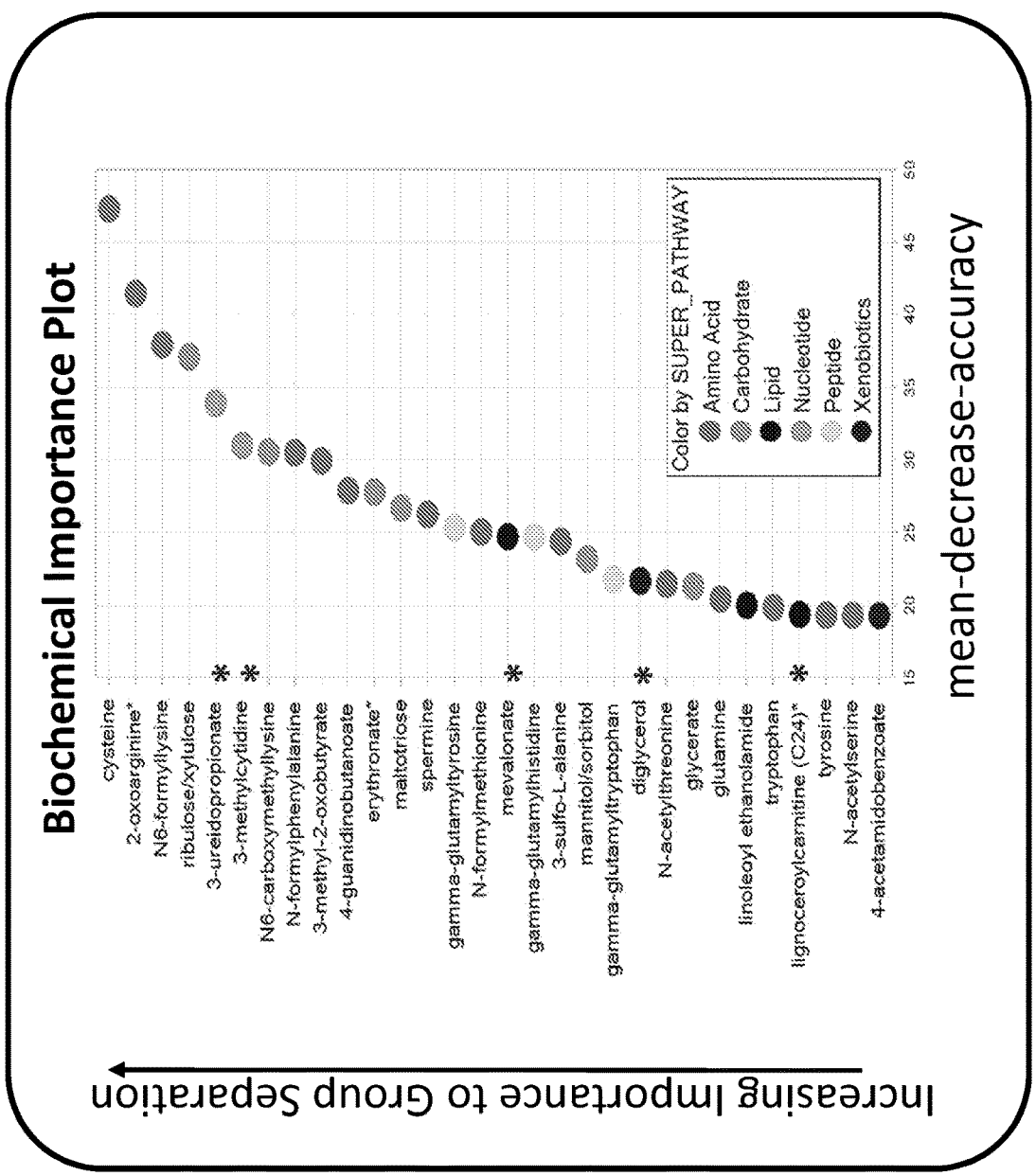

FIG. 8 shows a table of Random Forest classification of most discriminatory metabolites in fecal samples from seizure-protected (SPF KD+SPF AkkPb KD) versus seizure-unprotected (SPF CD+SPF Abx KD) mice. * denotes biomarkers that are elevated. Biomarkers without * were reduced.

Figure 9:
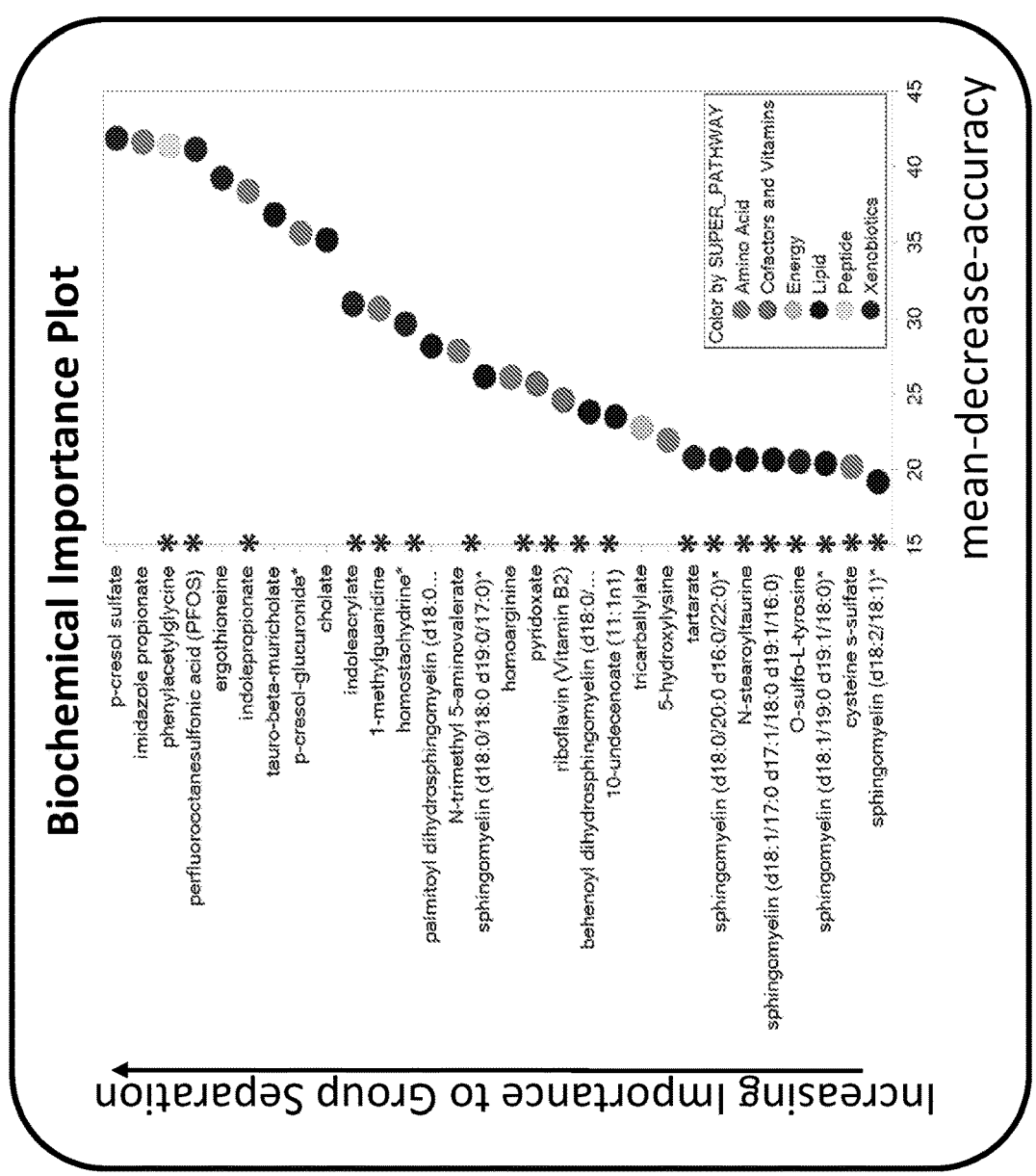

FIG. 9 shows a table of Random Forest classification of most discriminatory metabolites in serum samples from mice treated with or without antibiotics. * denotes biomarkers that are elevated. Biomarkers without * were reduced.

Figure 10:
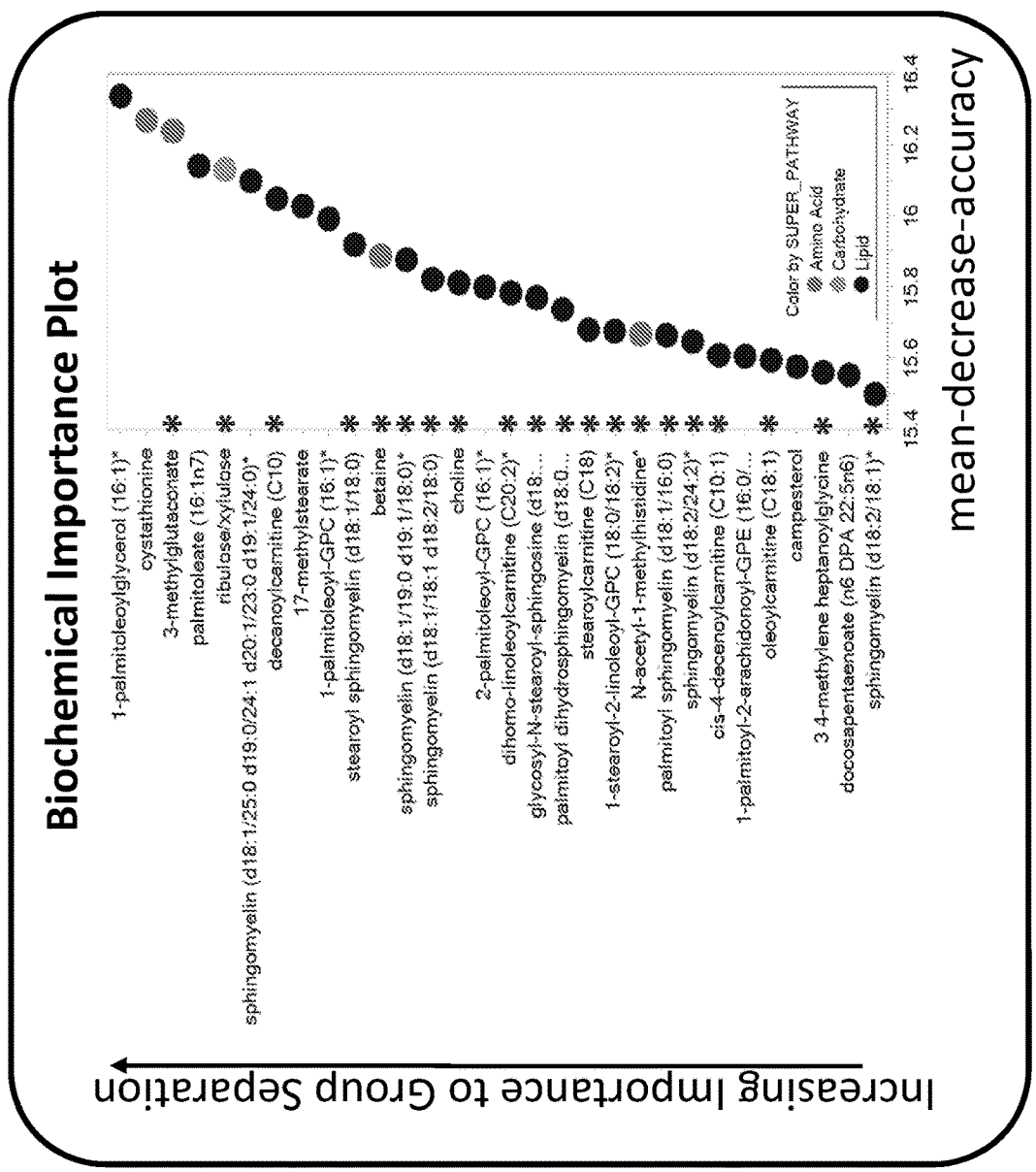

FIG. 10 shows a table of Random Forest classification of most discriminatory metabolites in serum samples from mice fed a control diet versus mice fed a ketogenic diet. * denotes biomarkers that are elevated. Biomarkers without * were reduced.

Figure 11:
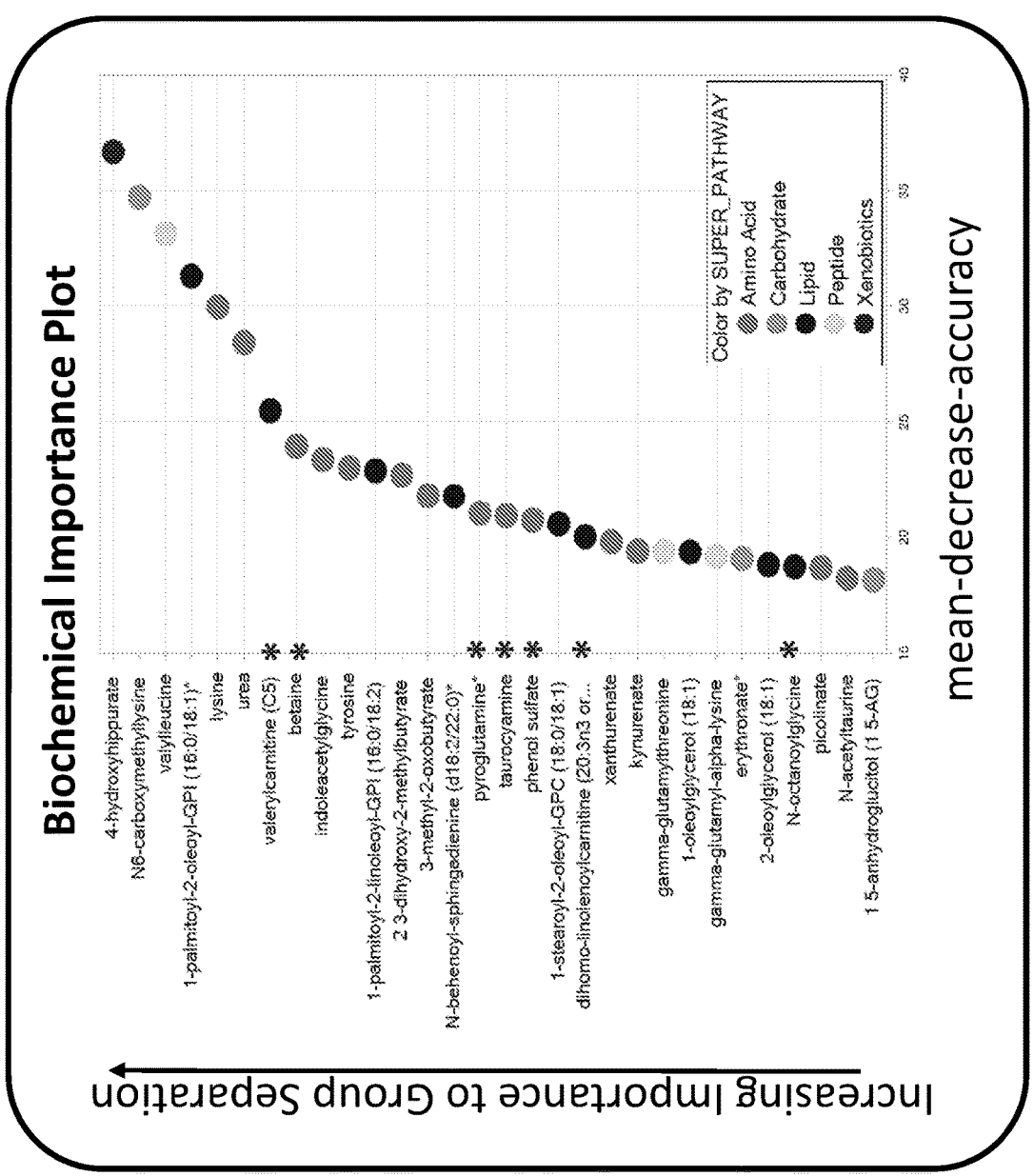

FIG. 11 shows a table of Random Forest classification of most discriminatory metabolites in serum samples from seizure-protected (SPF KD+SPF AkkPb KD) versus seizure-unprotected (SPF CD+SPF Abx KD) mice. * denotes biomarkers that are elevated. Biomarkers without * were reduced.

Figure 12:
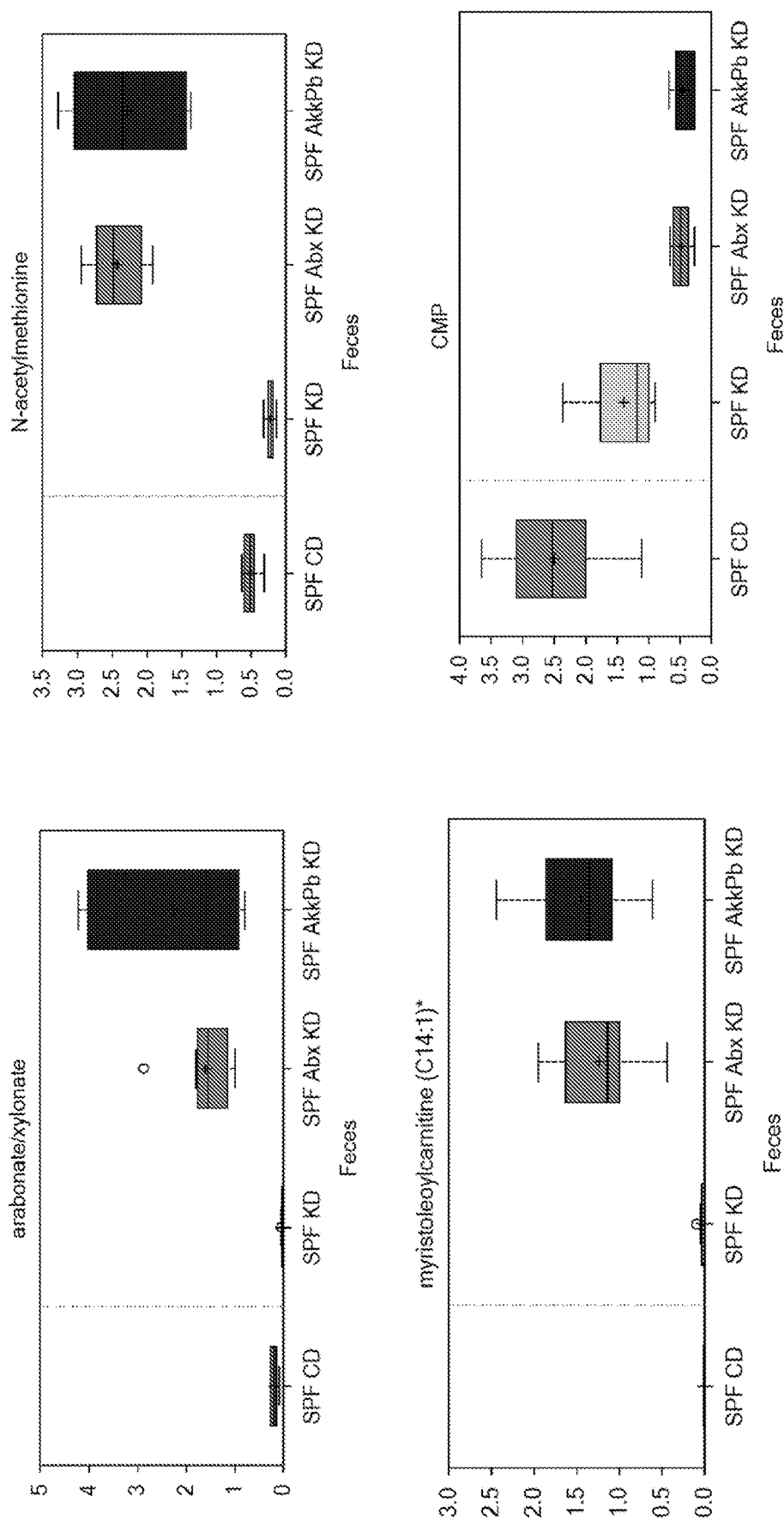
Figure 12:
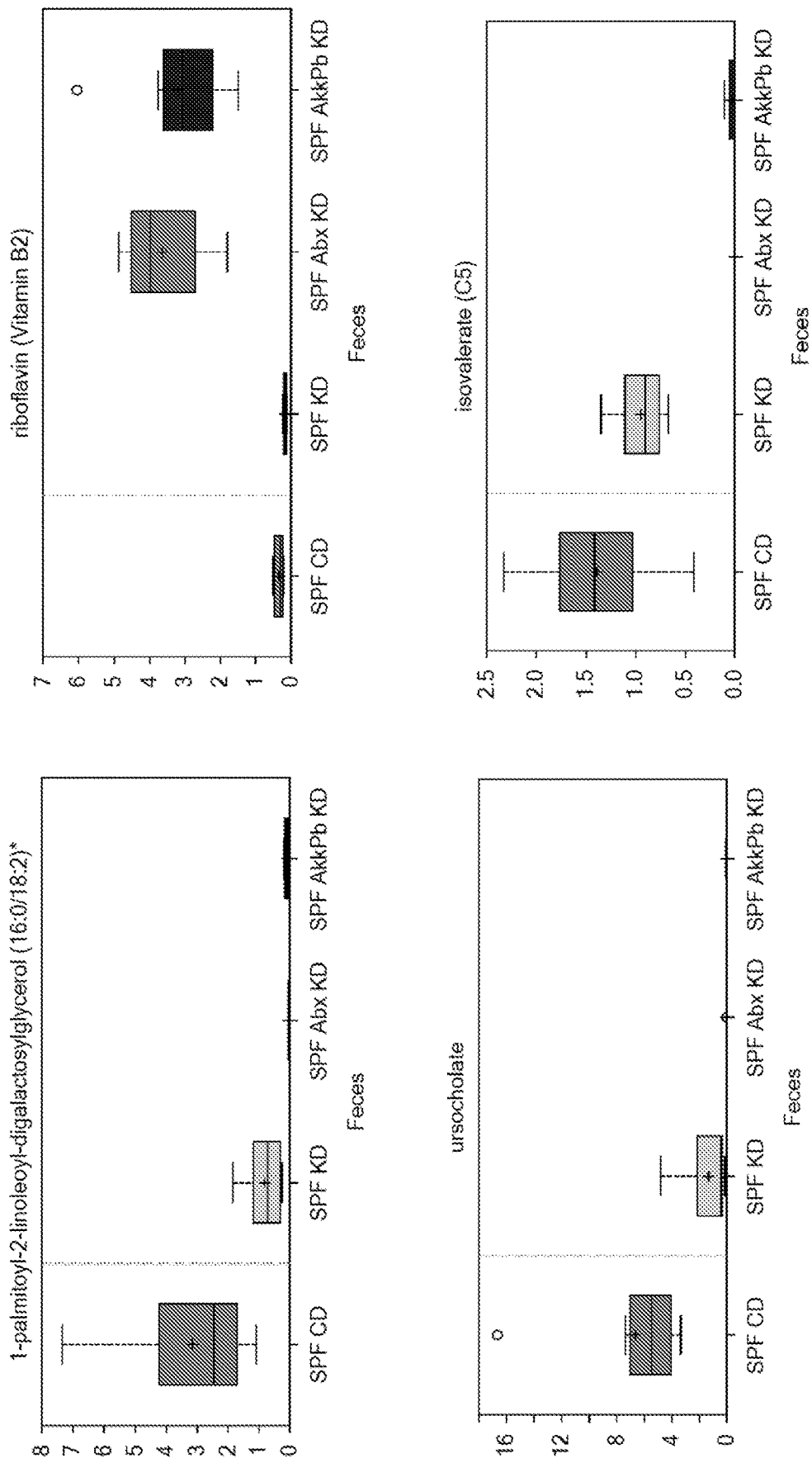
Figure 12:
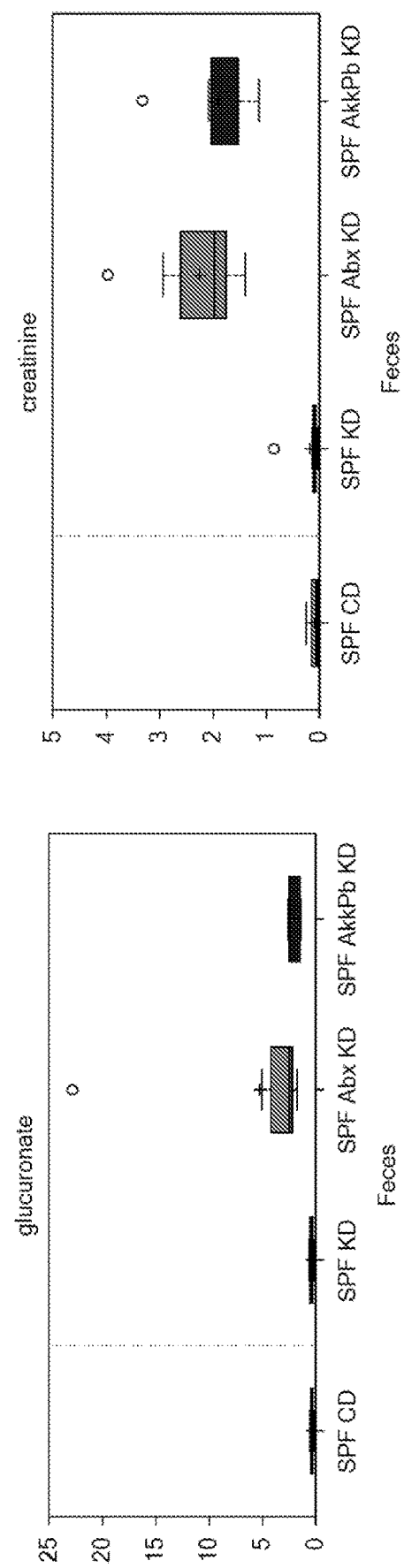

FIG. 12 shows box plots of most discriminatory metabolites in fecal samples from groups treated with and without antibiotics.

Figure 13:
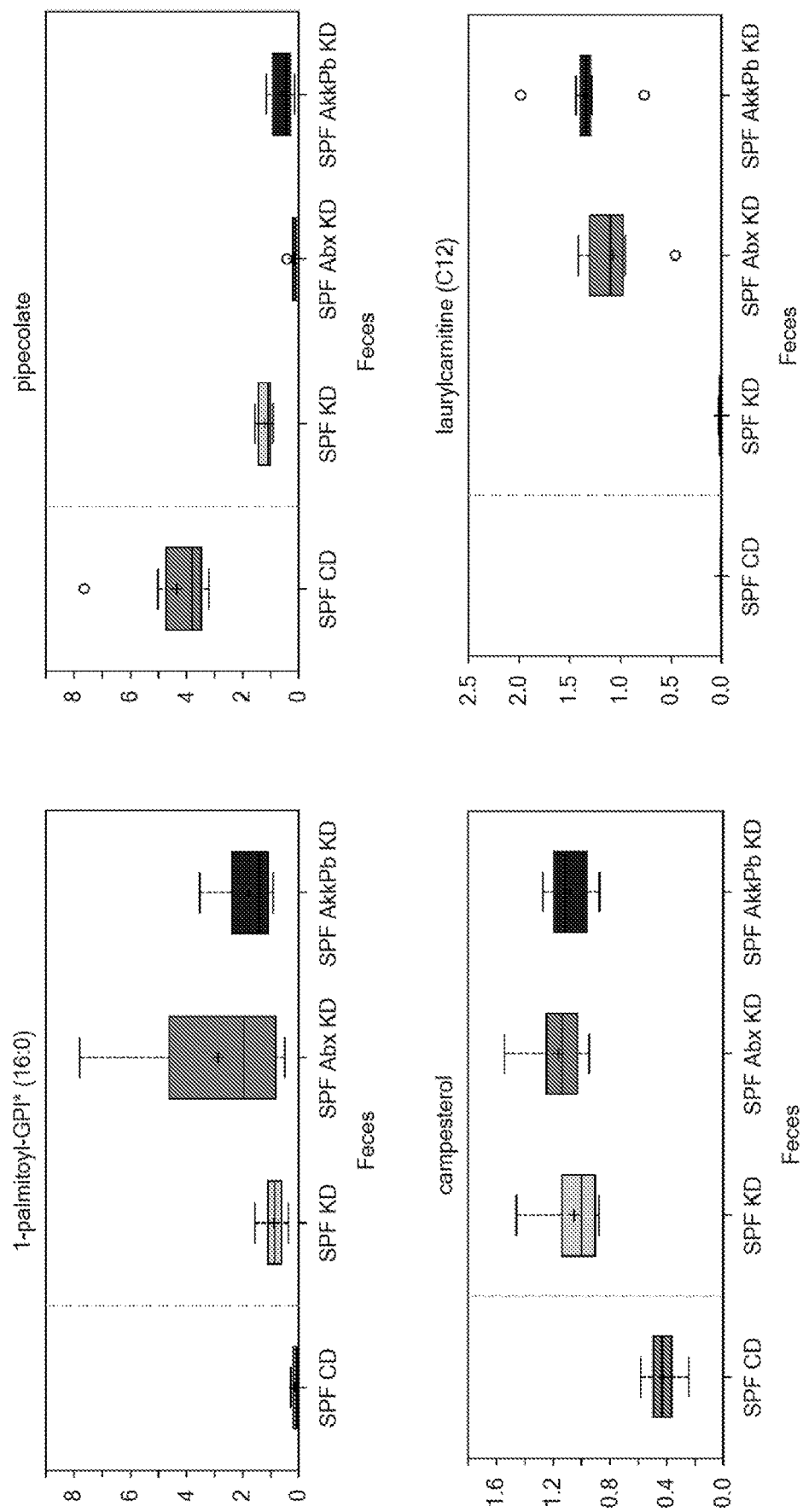
Figure 13:
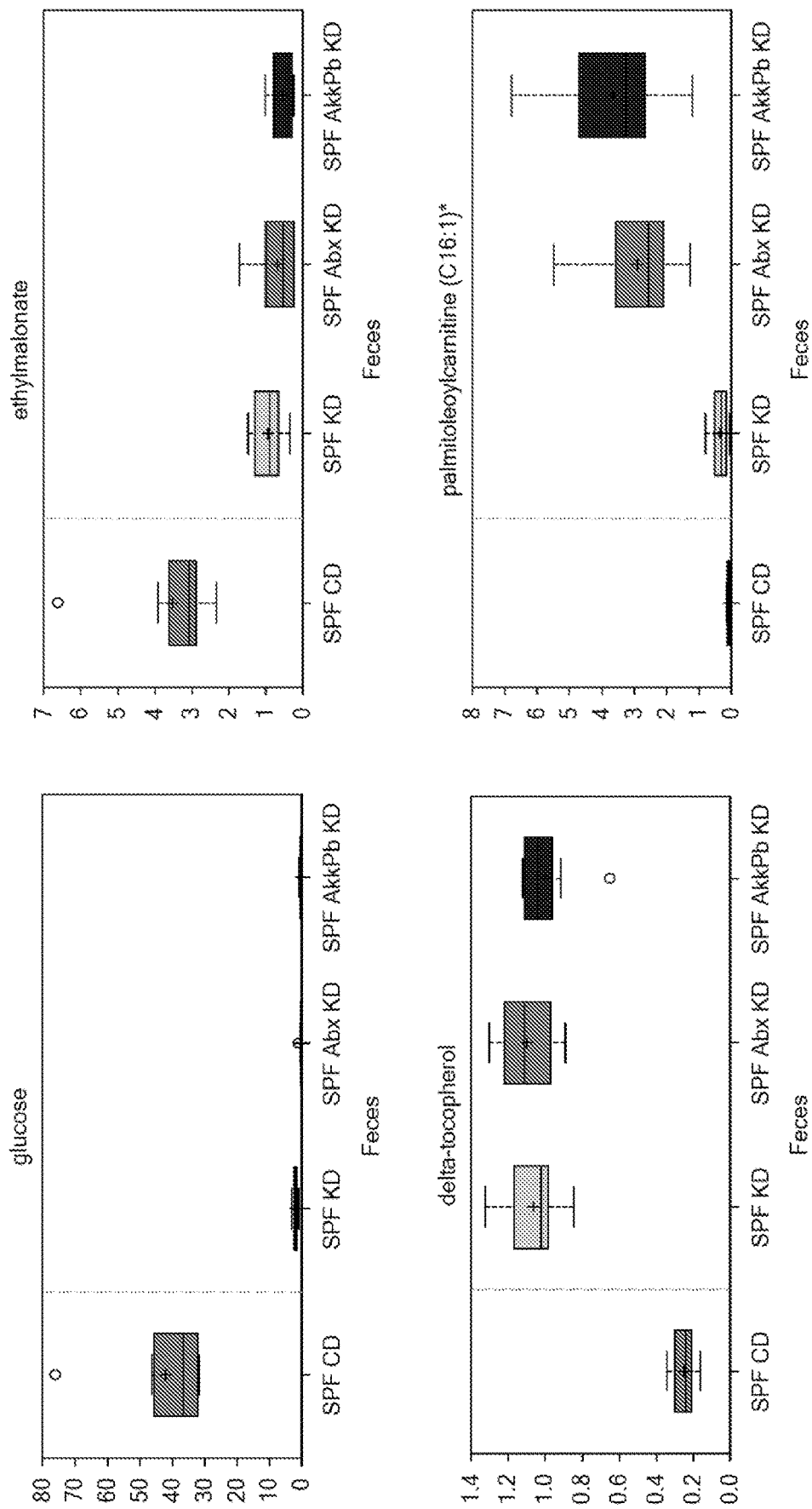
Figure 13:
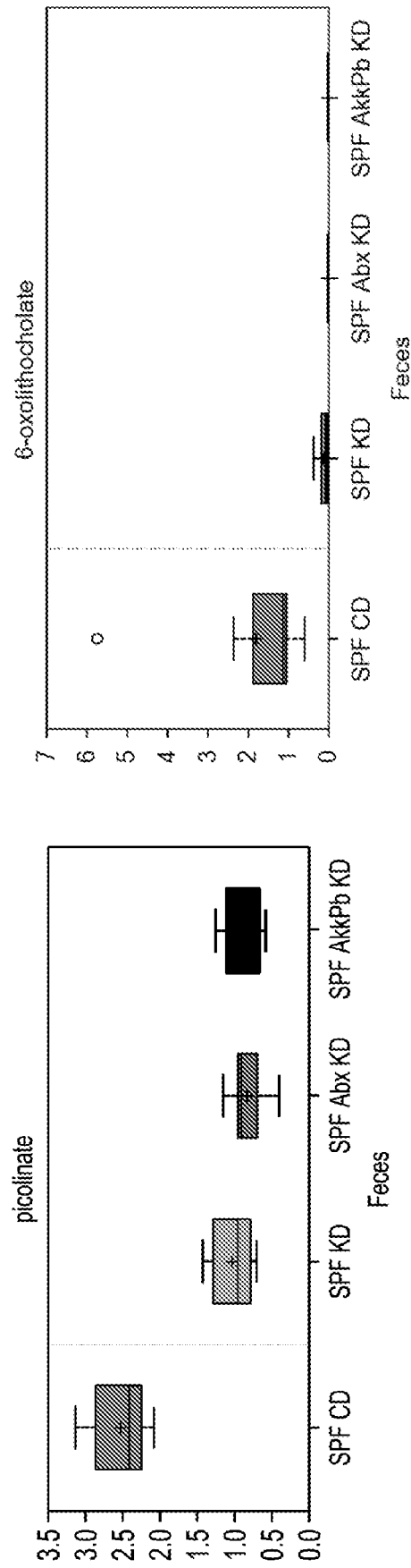

FIG. 13 shows box plots of most discriminatory metabolites in fecal samples from mice fed a control diet versus mice fed a ketogenic diet.

Figure 14:
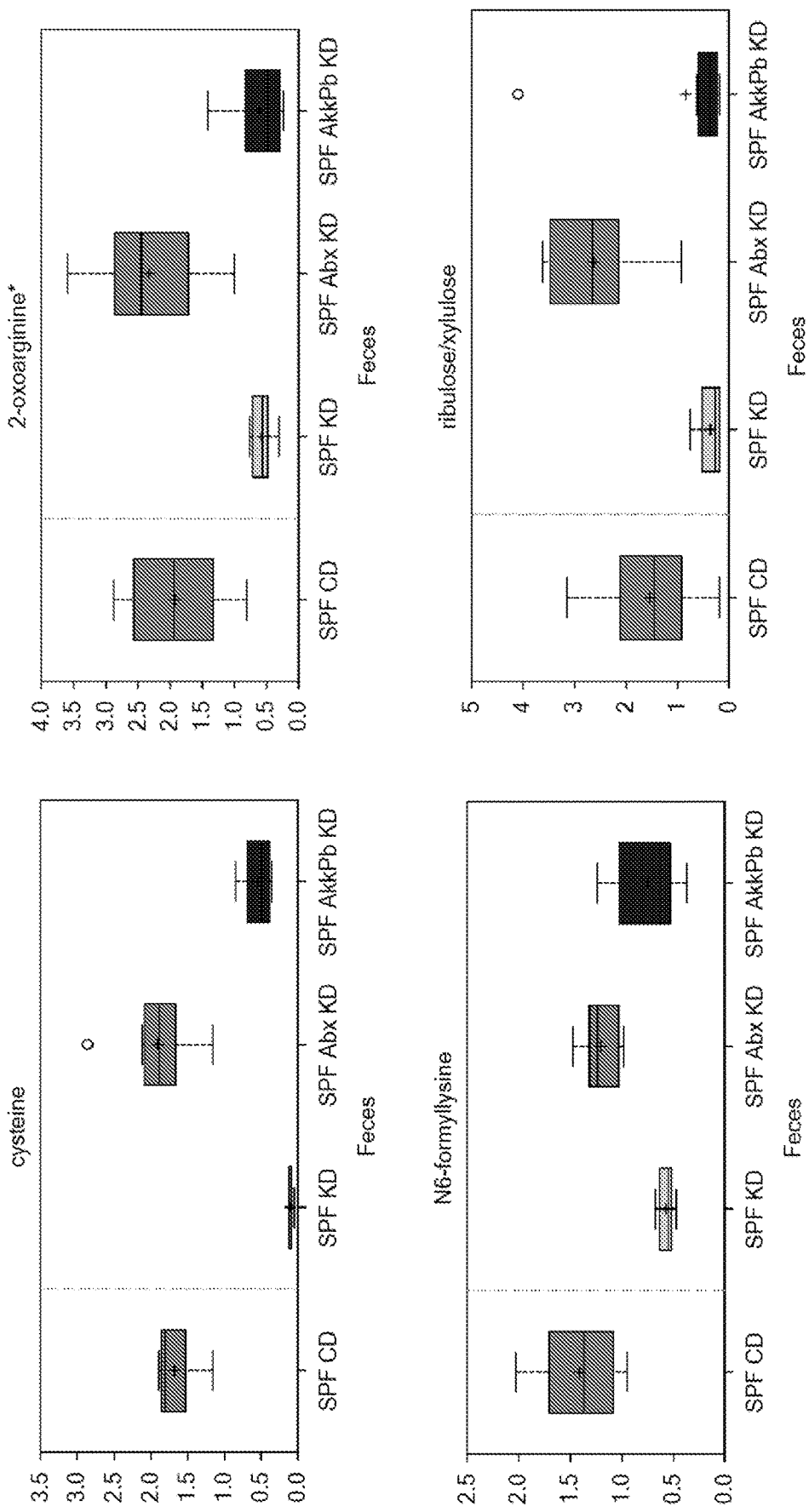
Figure 14:
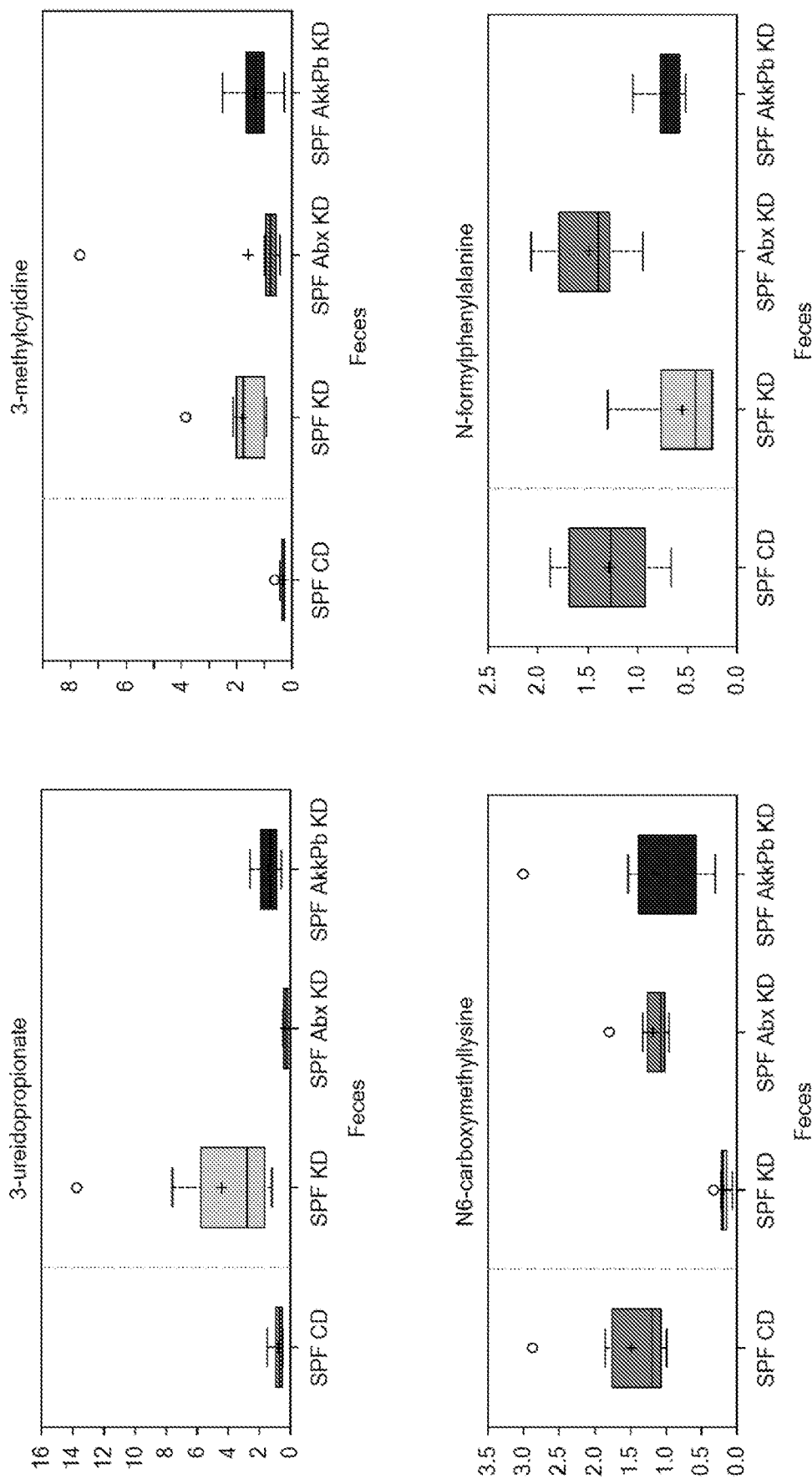
Figure 14:
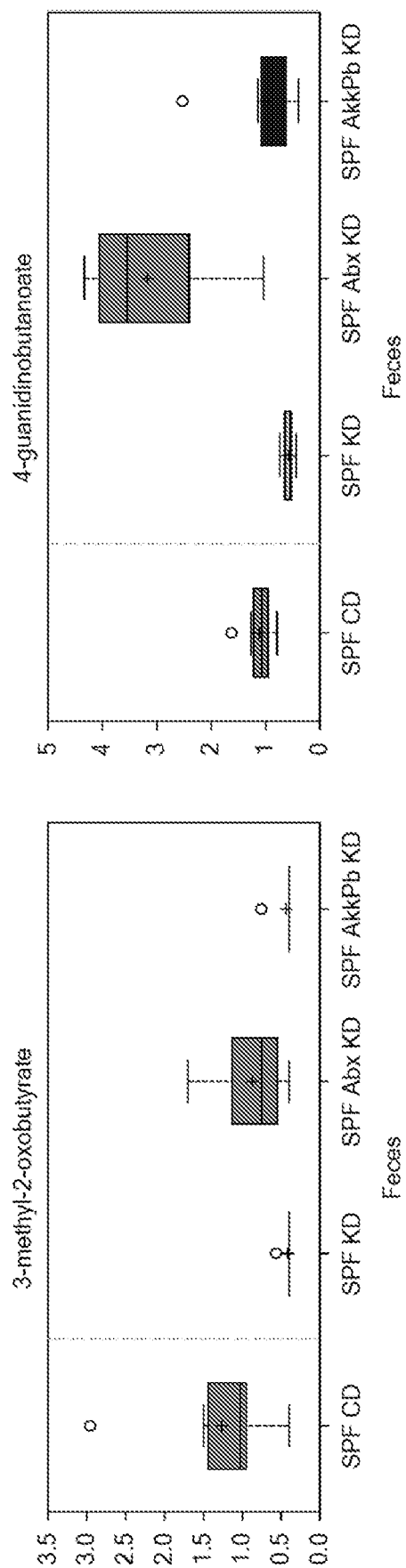

FIG. 14 shows box plots of most discriminatory metabolites in fecal samples from seizure-protected (SPF KD+SPF AkkPB KD) versus seizure-unprotected (SPF CD+SPF Abx KD) mice.

Figure 15:
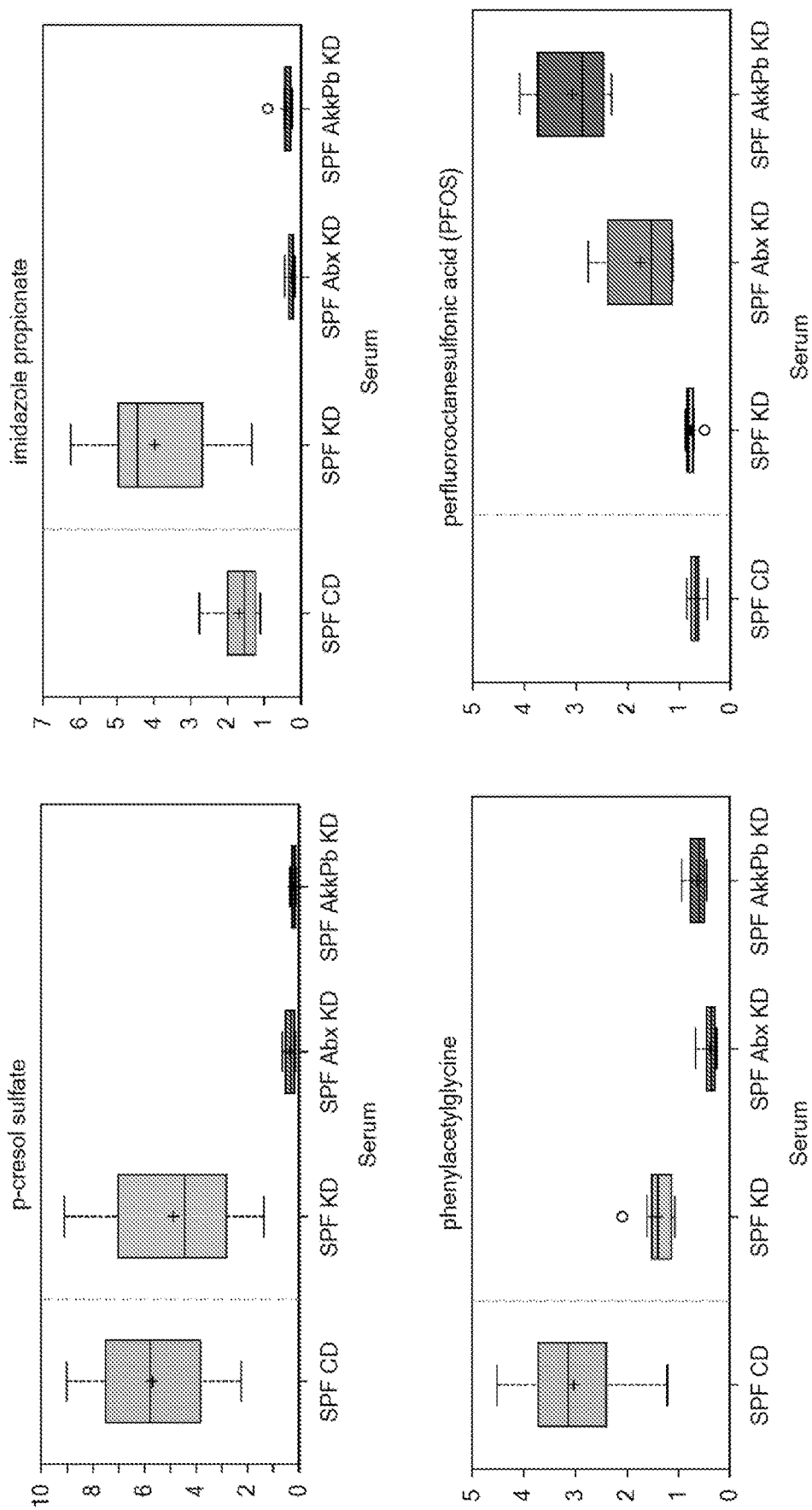
Figure 15:
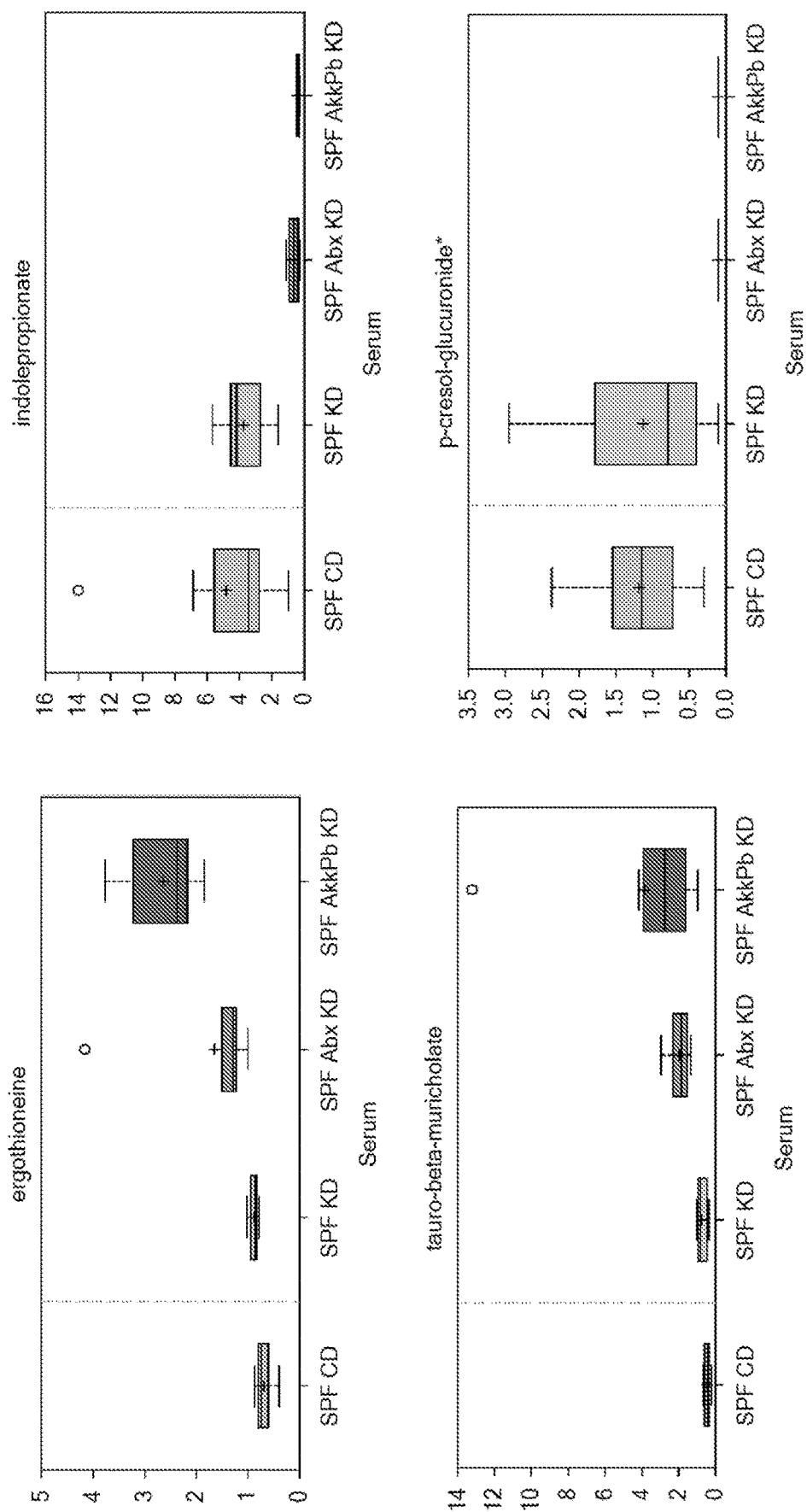
Figure 15:
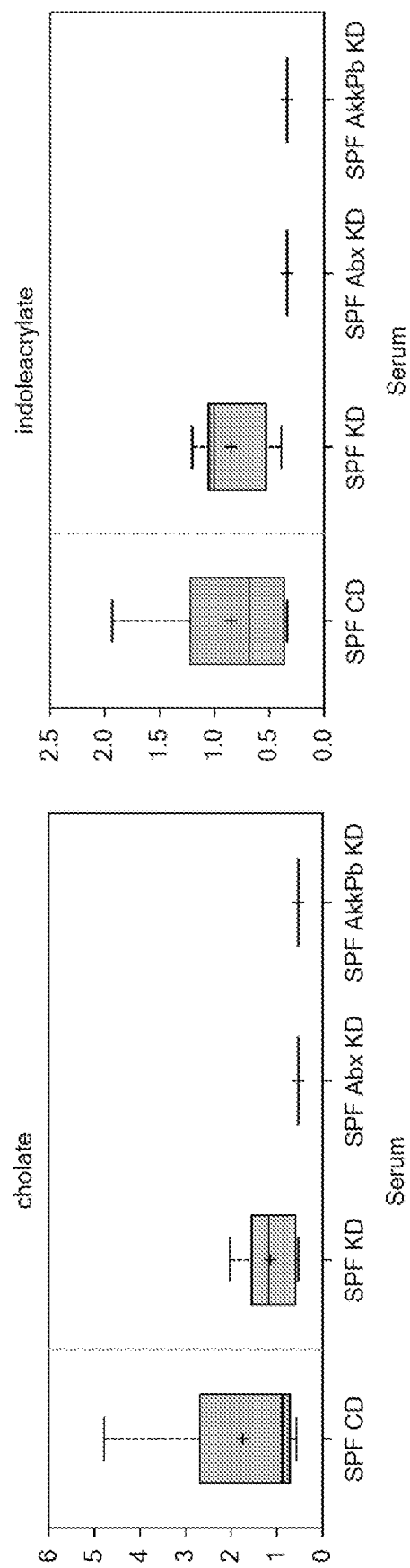

FIG. 15 shows box plots of most discriminatory metabolites in serum samples from mice treated with or without antibiotics.

Figure 16:
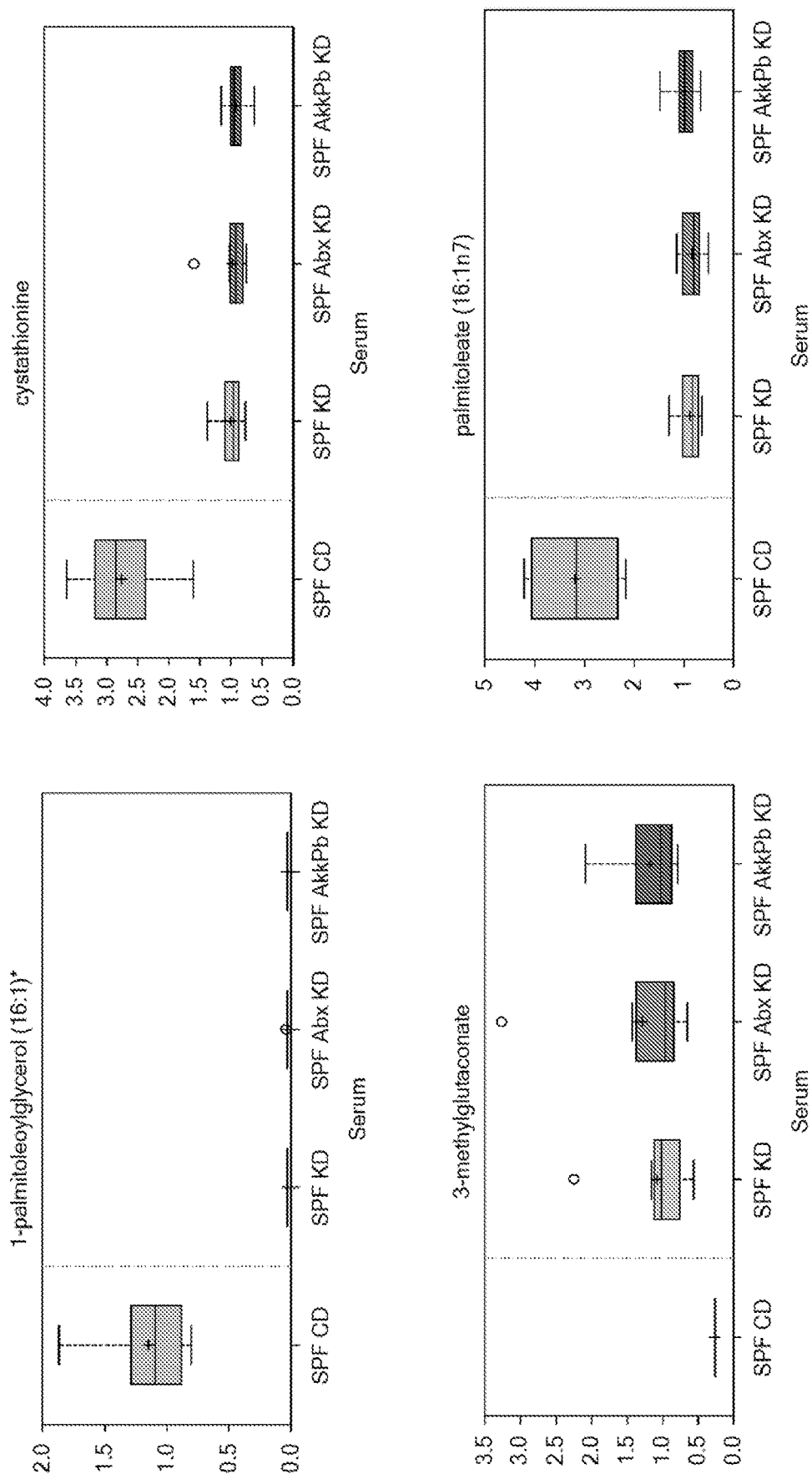
Figure 16:
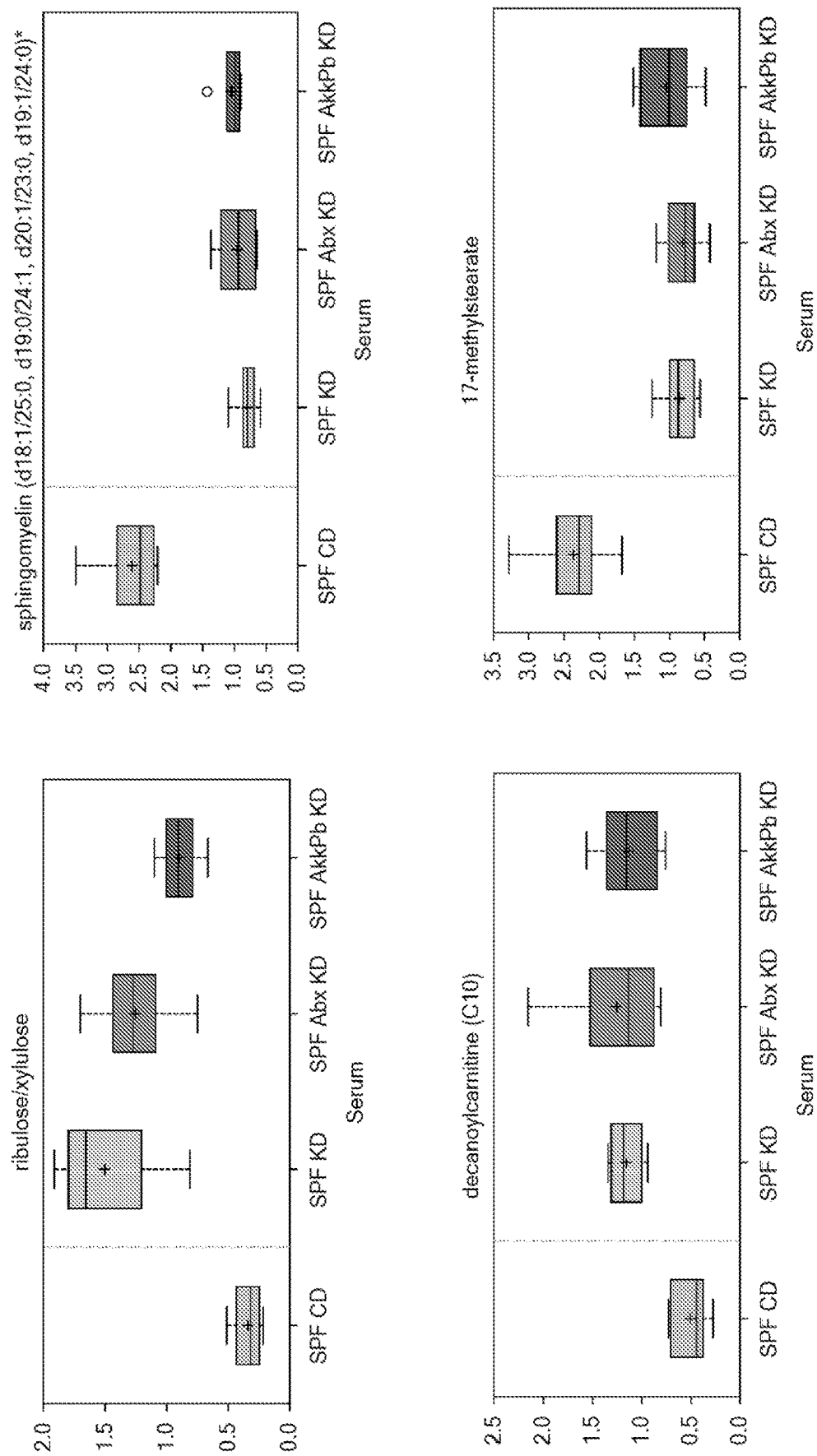
Figure 16:
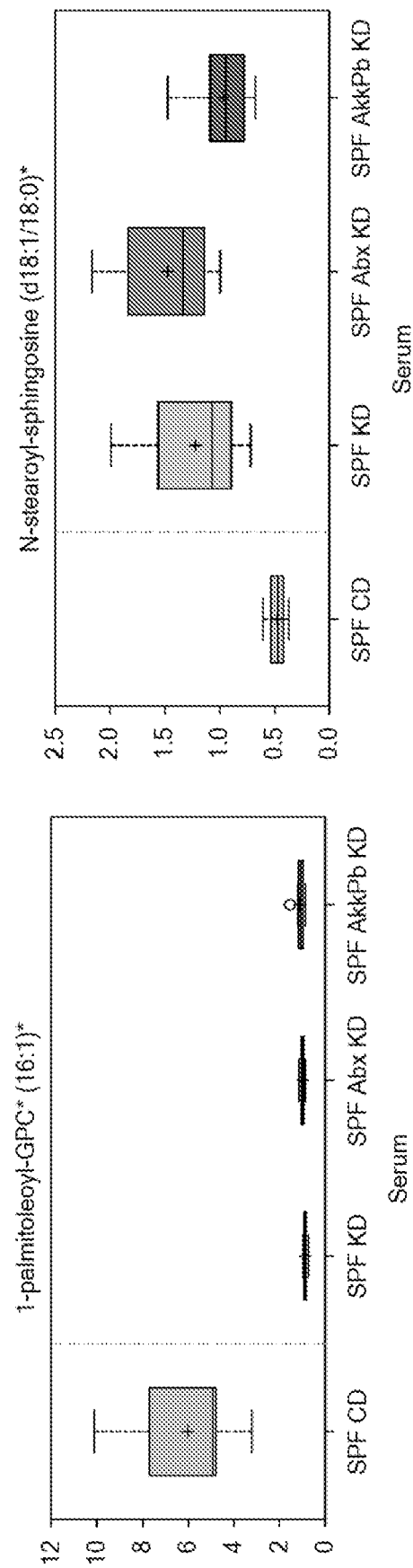

FIG. 16 shows box plots of most discriminatory metabolites in serum samples from mice fed a control diet versus mice fed a ketogenic diet.

Figure 17:
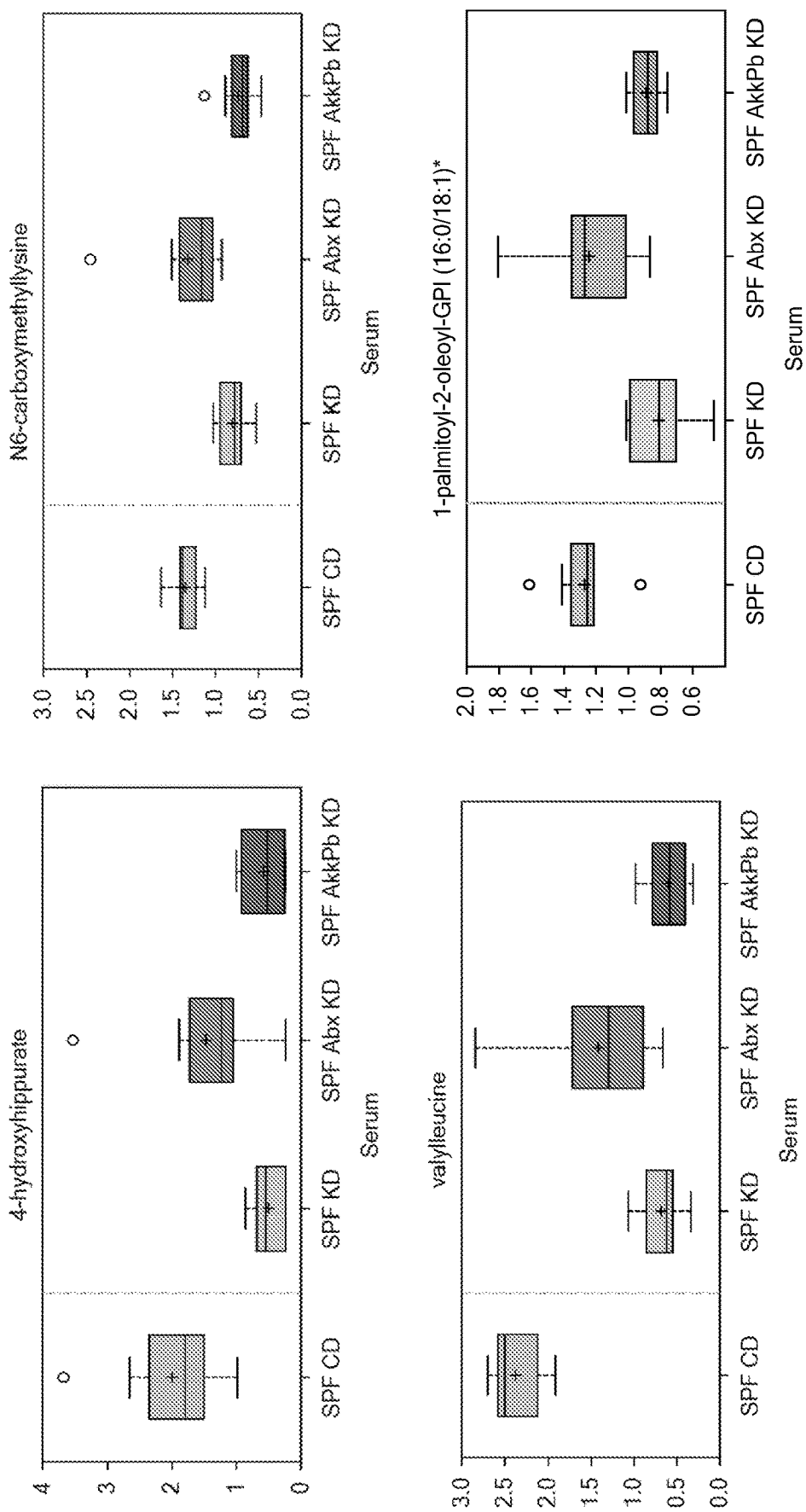
Figure 17:
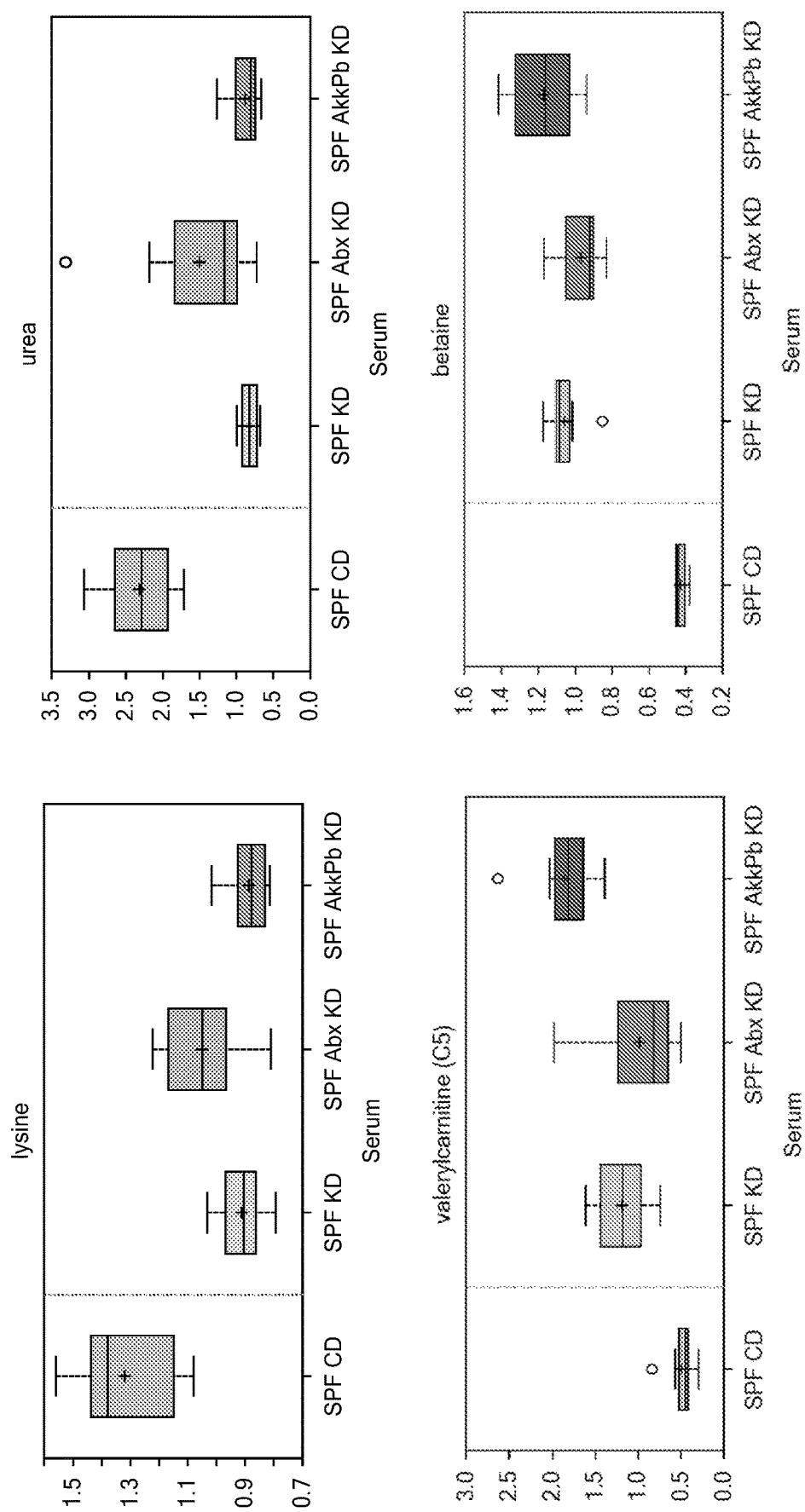
Figure 17:
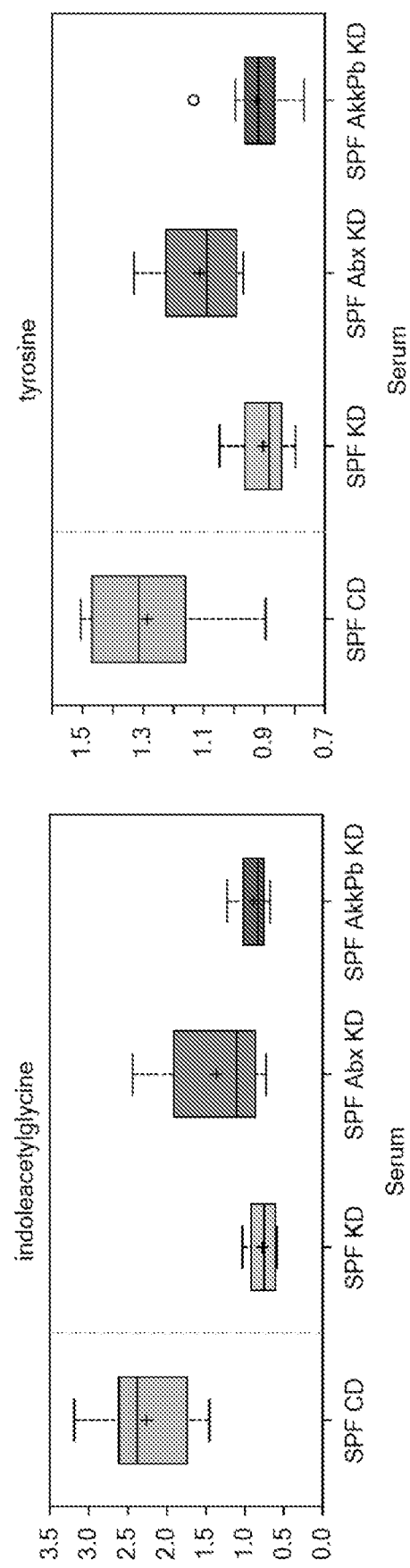

FIG. 17 shows box plots of most discriminatory metabolites in serum samples from seizure-protected (SPF KD+SPF AkkPb KD) versus seizure-unprotected (SPF CD+SPF Abx KD) mice.

DETAILED DESCRIPTION

Provided herein are methods for selecting a subject in need thereof for treatment with a composition that mimics the effects of a ketogenic diet, as well as methods of treating the subject, determining the efficacy of the treatment, and adjusting the treatment dosage and frequency.

Definitions

As used herein in the specification, "a" or "an" may mean one or more. As used herein in the claim(s), when used in conjunction with the word "comprising", the words "a" or "an" may mean one or more than one. As used herein "another" may mean at least a second or more.

As used herein, the term "biomarker" is anything that can be used as an indicator of a particular physiological state of an organism. For example, a biomarker can be the level(s) of a particular by-product, metabolite, mRNA or protein associated with a particular physiological state.

As used herein, the term "increase" can refer to a level including the reference level or cut-of-value or to an overall increase of 5%, 10%, 20%, 25%, 30%, 40%, 50%, 60%, 70%, 80%, 85%, 90%, 95%, 96%, 97%, 98, and 99% or greater, in biomarker level detected by the methods described herein, as compared to the level of the same biomarker from a reference sample. In certain embodiments, the term "decrease" refers to the decrease in biomarker level, wherein the decreased level is 0.1, 0.5, 1, 2, 3, 4, 5-fold or more than 5-fold lower compared to the level of the biomarker in a reference sample.

As used herein, the term "differs by" refers to a relative difference between two values. For example, if X differs by 10% relative to Y, then $|X-Y|/|Y|=0.1$, where the vertical bars (i.e., the pipes) denote the absolute values. Therefore, the term "differs by" encompasses both "differs by being higher" (e.g., $|110-100|/|100|=0.1$; for X=110 and Y=100) and "differs by being lower" (e.g., $|90-100|/|100|=0.1$; for X=90 and Y=100). In some embodiments that are described with respect to a value differing from another by a certain amount, it might be sufficient to make a mere binary determination of whether the difference is on one side or the other side of a threshold value rather than any more fine-grained determination (e.g., for an embodiment in which X must differ by being higher by at least 20% relative to Y, it might be sufficient to determine whether X differs by some amount that is higher than 20% instead of determining whether such a difference specifically is 60%, 90%, 120%, etc.). In embodiments that compare variables that are individually discrete or binary (e.g., presence, absence) rather than potentially continuous (e.g., amount, activity), the same "differs by" terminology can be used herein. In that case, if an individual measurement is compared, any non-zero difference in value indicates that the measurements are different (e.g., one is present, the other is absent). Again, in that case, if aggregate (rather than individual) measurements from a sample are compared, then the difference values indicate the population-level measurements (e.g., present at a level of 30 in the test sample vs. 60 in the reference sample (thereby differing by 50%), wherein the level can be the number of cells or any other measured metric).

As used herein, the phrase "at a reference level" refers to a biomarker level that is the same as the level of the same biomarker, detected by the methods described herein, from a reference sample, or that is a level representative of measurements from samples of a certain type.

The phrase "pharmaceutically-acceptable carrier" as used herein means a pharmaceutically-acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and in relation to a condition, such as a local recurrence, is well understood in the art, and includes administration of a composition that reduces the frequency of, or delays the onset of, symptoms of a medical condition in a subject relative to a subject who does not receive the composition. Thus, prevention of seizures includes, for example, reducing the number of seizures in a population of patients receiving a prophylactic treatment relative to an untreated control population, and/or delaying the appearance of detectable lesions in a treated population versus an untreated control population, e.g., by a statistically and/or clinically significant amount.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The term "subject" refers to a mammal, including, but not limited to, a human or non-human mammal, such as a bovine, equine, canine, ovine, or feline.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in a manner to improve or stabilize a subject's condition.

Methods of Selecting Subjects, Monitoring Efficacy, and Adjusting Dosage

The experiments in the Examples below show that the efficacy of a probiotic composition correlates with the level of ketogenic gamma-glutamylated amino acids and seizure susceptibility. The experiments show that metabolomic profiles in colonic lumenal contents and sera can discriminate seizure-protected from seizure-susceptible groups, with a predictive accuracy of 94% for colonic lumenal metabolites and 87.5% for serum metabolites. Thus, methods of determining the expression level of one or more biomarkers that contribute to lipid metabolism, carbohydrate metabolism, or amino acid metabolism can be used to select subjects for treatment with probiotic compositions that modulate these biochemical processes.

Biomarkers for Selecting Subjects for Treatment

The methods for selecting subjects for treatment with a probiotic composition that modulates gut, serum, and brain metabolomes can include detecting the level of a biomarker of FIG. 8. In some embodiments, the methods include assaying 5, 10, 20, 25, or all 30 biomarkers.

Methods of Detecting Biomarkers

The methods disclosed herein can include detecting levels of a biomarker, in a subject or a biological sample obtained from the subject, and comparing them to a reference sample. Detecting alterations in the expression level of a biomarker can include measuring the level of protein or mRNA of the biomarker and comparing it to a control. Additionally, or alternatively, the methods can include genotyping or haplotyping the gene encoding the biomarker in a subject or a biological sample obtained from the subject, and comparing it to a control. In some embodiments, the biological sample is one that is isolated from the subject.

Biological Samples

A biological sample can be obtained from an individual for use in the methods disclosed herein. The biological sample can be a biological fluid sample take from a subject. Examples of biological samples include urine, barbotage, blood, serum, plasma, tears, saliva, cerebrospinal fluid, tissue, lymph, synovial fluid, or sputum, etc. A biological fluid sample can be whole blood, or more preferably serum or plasma. Serum is the component of whole blood that is neither a blood cell (serum does not contain white or red blood cells) nor a clotting factor. It is the blood plasma with the fibrinogens removed. Accordingly, serum includes all proteins not used in blood clotting (coagulation) and all the electrolytes, antibodies, antigens, hormones, and any exogenous substances (e.g., drugs and microorganisms). The sample can be diluted with a suitable diluent before the sample is analyzed.

In some embodiments, the sample is a fecal sample obtained from the subject. The sample may be obtained from the subject using a variety of methods that are known in the art.

As discussed in more detail below, the subject can be one with a disorder in need of treatment. For example, the subject may have a neurodevelopmental disorder, such as an autism spectrum disorder, Rett syndrome, fragile X, attention deficit disorder (ADD), attention-deficit/hyperactivity disorder (ADHD), refractory epilepsy, and/or non-refractory epilepsy.

Controls

The methods disclosed herein typically include comparing the level of the biomarker detected in a sample obtained from the subject to a reference level, e.g., a level representative of a reference sample or samples. A suitable reference sample will be known to one of skill in the art. Reference samples can include, for example, samples obtained from healthy subjects, such as subjects without the disease or disorder. The reference biological sample(s) can be assayed using the same methods as the test sample.

Therapeutic Methods

Provided herein are methods of treating or preventing seizures in a subject. In some embodiments, the methods relate to treating or preventing seizures in the subject by administering a composition comprising bacteria of *Akkermansia* and *Parabacteroides* genera. In some aspects, the methods provided herein relate to treating or preventing seizures in a subject by depleting the gut microbiota of the subject and administering a composition comprising bacteria of *Akkermansia* genus (e.g., *Akkermansia muciniphila*) and *Parabacteroides* genus (e.g., *Parabacteroides merdae* or *Parabacteroides distasonis*) to the subject. In some embodiments, the subject has epilepsy. (e.g., refractory or non-refractory epilepsy). In some embodiments, the subject has a neurodevelopmental disorder. Representative neurodevelopmental disorders include autism spectrum disorder, Rett syndrome, fragile X, attention deficit disorder, and attention-deficit/hyperactivity disorder. In some embodiments, the neurodevelopmental disorder is a disorder known to be comorbid with seizures. The composition may be formulated for oral delivery. In some embodiments, the composition may comprise probiotics. In some embodiments, the compositions disclosed herein are food products. The composition may be in the form of a pill, tablet, or capsule. In some embodiments, the subject may be a mammal (e.g., a human). In some embodiments, the composition is self-administered.

In some embodiments, the composition is formulated for rectal delivery (e.g., a fecal sample). In some embodiments, the subject undergoes fecal microbiota transplant, wherein the transplant comprises a composition disclosed herein. Fecal microbiota transplantation (FMT), also commonly known as 'fecal bacteriotherapy' represents a therapeutic protocol that allows the reconstitution of colon microbial communities. The process involves the transplantation of fecal bacteria from a healthy individual into a recipient. FMT restores colonic microflora by introducing healthy bacterial flora through infusion of a fecal sample, e.g. by enema, orogastric tube or by mouth in the form of a capsule containing freeze-dried material, obtained from a healthy donor. In some embodiments, the fecal sample is from a fecal bank.

In some embodiments, the bacterial DNA in subject's gut microbiota is sequenced. The subject's gut bacterial DNA may be sequenced prior to administration of the composition. For example, a sample comprising bacterial DNA may be obtained from the subject, and the bacterial DNA is then sequenced for *Akkermansia* (Akk) and/or *Parabacteroides* DNA, therefore measuring the presence or level of *Akkermansia* and/or *Parabacteroides* in the subject's gut microbiota. The composition disclosed herein may then be administered to the subject if the level of *Akkermansia* and/or *Parabacteroides* is low. In some embodiments, the subject is deemed to have low levels of *Akkermansia* and/or *Parabacteroides* if less than 0.0001%, less than 0.001%, less than 0.01%, less than 0.02%, less than 0.03%, less than 0.04%, less than 0.05%, less than 0.06% less than 0.07%, less than 0.08%, less than 0.09%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 5%, less than 7%, less than 10%, less than 20%, less than 30%, less than 40%, or less than 50% of the bacteria in the sample is *Akkermansia* and/or *Parabacteroides* DNA. Bacterial DNA to be sequenced may be obtained through any means known in the art, including, but not limited to, obtaining a fecal sample from the subject and isolating the bacterial DNA. Bacterial DNA sequencing by any known technique in the art, including, but not limited to, Maxam Gilbert sequencing, Sanger sequencing, shotgun sequencing, bridge PCR, or next generation sequencing methods, such as massively parallel signature sequencing (MPSS), polony sequencing, 454 pyrosequencing, Illumina (Solexa) sequencing, SOLiD sequencing, Ion torrent semiconductor sequencing, DNA nanoball sequencing, heliscope single molecule sequencing, single molecule real time (SMRT) sequencing, or nanopore DNA sequencing.

In some embodiments, the above methods directly act to reduce the amount of pathogenic bacteria in a subject (i.e., in the gastrointestinal tract of the subject). In some embodiments, this includes any such therapy that achieves the same goal of reducing the number of pathogenic organisms, when used in combination with the compositions described herein, would lead to replacement of the pathogenic microflora involved in the diseased state with natural microflora associated with a non-diseased state, or less pathogenic species occupying the same ecological niche as the type causing a disease state. For example, a subject may undergo treatment with antibiotics (e.g., antimicrobial compounds) or a composition comprising antibiotics to target and decrease the prevalence of pathogenic organisms, and subsequently be treated with a composition described herein. The treatment may also comprise an antifungal or anti-viral compound.

Suitable antimicrobial compounds include capreomycins, including capreomycin IA, capreomycin IB, capreomycin IIA and capreomycin IIB; carbomycins, including carbomycin A; carumonam; cefaclor, cefadroxil, cefamandole, cefatrizine, cefazedone, cefazolin, cefbuperazone, cefcapene pivoxil, cefclidin, cefdinir, cefditoren, cefime, ceftamet, cefmenoxime, cefmetzole, cefminox, cefodizime, cefonicid, cefoperazone, ceforanide, cefotaxime, cefotetan, cefotiam, cefoxitin, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephalexin, cephalogycin, cephaloridine, cephalosporin C, cephalothin, cephapirin, cephamycins, such as cephamycin C, cephradine, chlortetracycline; chlarithromycin, clindamycin, clometocillin, clomocycline, cloxacillin, cyclacillin, danofloxacin, demeclocyclin, destomycin A, dicloxacillin, dirithromycin, doxycyclin, epicillin, erythromycin A, ethanbutol, fenbenicillin, flomoxef, florfenicol, floxacillin, flumequine, fortimicin A, fortimicin B, forfomycin, foraltadone, fusidic acid, gentamycin, glyconiazide, guamecycline, hetacillin, idarubicin, imipenem, isepamicin, josamycin, kanamycin, leumycins such as leumycin A1, lincomycin, lomefloxacin, loracarbef, lymecycline, meropenam, metampicillin, methacycline, methicillin, mezlocillin, micronomicin, midecamycins such as midecamycin A1, mikamycin, minocycline, mitomycins such as mitomycin C, moxalactam, mupirocin, nafcillin, netilicin, norcardians such as norcardian A, oleandomycin, oxytetracycline, panipenam, pazufloxacin, penamecillin, penicillins such as penicillin G, penicillin N and penicillin O, penillic acid, pentylpenicillin, peplomycin, phenethicillin, pipacyclin, piperacilin, pirlimycin, pivampicillin, pivcefalexin, porfiromycin, propiallin, quinacillin, ribostamycin, rifabutin, rifamide, rifampin, rifamycin SV, rifapentine, rifaximin, ritipenem, rekitamycin, rolitetracycline, rosaramicin, roxithromycin, sancycline, sisomicin, sparfloxacin, spectinomycin, streptozocin, sulbenicillin, sultamicillin, talampicillin, teicoplanin, temocillin, tetracyclin, thostrepton, tiamulin, ticarcillin, tigemonam, tilmicosin, tobramycin, tropospectromycin, trovafloxacin, tylosin, and vancomycin, and analogs, derivatives, pharmaceutically acceptable salts, esters, prodrugs, and protected forms thereof Suitable anti-fungal compounds include ketoconazole, miconazole, fluconazole, clotrimazole, undecylenic acid, sertaconazole, terbinafine, butenafine, clioquinol, haloprogin, nystatin, naftifine, tolnaftate, ciclopirox, amphotericin B, or tea tree oil and analogs, derivatives, pharmaceutically acceptable salts, esters, prodrugs, and protected forms thereof.

Suitable antiviral agents include acyclovir, azidouridine, anismoycin, amantadine, bromovinyldeoxusidine, chlorovinyldeoxusidine, cytarabine, delavirdine, didanosine, deoxynojirimycin, dideoxycytidine, dideoxyinosine, dideoxynucleoside, desciclovir, deoxyacyclovir, efavirenz, enviroxime, fiacitabine, foscamet, fialuridine, fluorothymidine, floxuridine, ganciclovir, hypericin, idoxuridine, interferon, interleukin, isethionate, nevirapine, pentamidine, ribavirin, rimantadine, stavudine, sargramostin, suramin, trichosanthin, tribromothymidine, trichlorothymidine, trifluorothymidine, trisodium phosphomonoformate, vidarabine, zidoviridine, zalcitabine and 3-azido-3-deoxythymidine and analogs, derivatives, pharmaceutically acceptable salts, esters, prodrugs, and protected forms thereof.

Other suitable antiviral agents include 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), 2'-deoxy-3'-thia-cytosine (3TC or lamivudine), 2',3'-dideoxy-T-fluoroadenosine, 2',3'-dideoxy-T-fluoroinosine, 2',3'-dideoxy-1'-fluorothymidine, 2',3'-dideoxy-2'-fluorocytosine, 2'3'-dideoxy-2',3'-didehydro-2'-fluorothymidine (Fd4T), 2'3'-dideoxy-2'-beta-fluoroadenosine (F-ddA), 2'3'-dideoxy-2'-beta-fluoroinosine (F-ddI), and 2',3'-dideoxy-2'-beta-flurocytosine (F-ddC). In some embodiments, the antiviral agent is selected from trisodium phosphomonoformate, ganciclovir, trifluorothymidine, acyclovir, 3'-azido-3'-thymidine (AZT), dideoxyinosine (ddI), and idoxuridine and analogs, derivatives, pharmaceutically acceptable salts, esters, prodrugs, and protected forms thereof.

Compositions

In some aspects, the invention relates to a composition (e.g., a food product or a pharmaceutical composition) comprising bacteria of *Akkermansia* (Akk) and *Parabacteroides* (Pb) genera. The composition may comprise a pharmaceutically acceptable carrier. The composition may comprise probiotics. The pharmaceutical compositions disclosed herein may be delivered by any suitable route of administration, including orally, buccally, sublingually, parenterally, and rectally, as by powders, ointments, drops, liquids, gels, tablets, capsules, pills, or creams. In certain embodiments, the pharmaceutical compositions are delivered generally (e.g., via oral administration). In certain other embodiments, the compositions disclosed herein are delivered rectally.

The composition may comprise any species of *Parabacteroides*, including, but not limited to, *P. chartae, P. chinchillae, P. distasonis, P. faecis, P. goldsteinii, P. gordonii, P. johnsonii,* or *P. merdae*. In some embodiments, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, of the bacteria in the composition are

*Parabacteroides* (Pb) bacteria. The bacteria of *Akkermansia* in the composition may comprise *Akkermansia muciniphila*. In some embodiments, the compositions disclosed herein may comprise at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% *Akkermansia* bacteria.

Compositions described herein may be used for oral administration to the gastrointestinal tract, directed at the objective of introducing the bacteria (e.g., the bacteria disclosed herein) to tissues of the gastrointestinal tract. The formulation for a composition (e.g., a probiotic composition) of the present invention may also include other probiotic agents or nutrients that promote spore germination and/or bacterial growth. An exemplary material is a bifidogenic oligosaccharide, which promotes the growth of beneficial probiotic bacteria. In some embodiments, the probiotic bacterial composition is administered with a therapeutically-effective dose of an (preferably, broad spectrum) antibiotic, or an anti-fungal agent. In some embodiments, the compositions described herein are encapsulated into an enterically-coated, time-released capsule or tablet. The enteric coating allows the capsule/tablet to remain intact (i.e., undissolved) as it passes through the gastrointestinal tract, until after a certain time and/or until it reaches a certain part of the GI tract (e.g., the small intestine). The time-released component prevents the "release" of the probiotic bacterial strain in the compositions described herein for a pre-determined time period.

The composition may be a food product, such as, but not limited to, a dairy product. The diary product may be cultured or a non-cultured (e.g., milk) dairy product. Non-limiting examples of cultured dairy products include yogurt, cottage cheese, sour cream, kefir, buttermilk, etc. Dairy products also often contain various specialty dairy ingredients, e.g. whey, non-fat dry milk, whey protein concentrate solids, etc. The dairy product may be processed in any way known in the art to achieve desirable qualities such as flavor, thickening power, nutrition, specific microorganisms and other properties such as mold growth control. The compositions of the present invention may also include known antioxidants, buffering agents, and other agents such as coloring agents, flavorings, vitamins, or minerals.

In some embodiments, the compositions of the present invention are combined with a carrier (e.g., a pharmaceutically acceptable carrier) which is physiologically compatible with the gastrointestinal tissue of the subject(s) to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration. The therapeutic composition of the present invention may also include a variety of carriers and/or binders. In some embodiments, the carrier is micro-crystalline cellulose (MCC) added in an amount sufficient to complete the one gram dosage total weight. Carriers can be solid-based dry materials for formulations in tablet, capsule or powdered form, and can be liquid or gel-based materials for formulations in liquid or gel forms, which forms depend, in part, upon the routes of administration. Typical carriers for dry formulations include, but are not limited to trehalose, maltodextrin, rice flour, microcrystalline cellulose (MCC) magnesium sterate, inositol, FOS, GOS, dextrose, sucrose, and like carriers. Suitable liquid or gel-based carriers include but are not limited to water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). Other carriers or agents for administering the compositions described herein are known in the art, e.g., in U.S. Pat. No. 6,461,607.

In some embodiments, the composition further comprises other bacteria or microorganisms known to colonize the gastrointestinal tract. For example, the composition may comprise species belonging to the Firmicutes phylum, the Proteobacteria phylum, the Tenericutes phylum, the Actinobacteria phylum, or a combination thereof. Examples of additional bacteria and microorganisms that may be included in the subject compositions include, but are not limited to, Saccharomyces, Bacteroides, Eubacterium, Clostridium, Lactobacillus, Fusobacterium, Propionibacterium, Streptococcus, Enteroccus, Lactococcus and Staphylococcus, Peptostreptococcus. In certain embodiments, the composition is substantially free of bacteria that increase the risk of seizures. Such bacteria include Bifidobacterium bacteria. Thus, in some embodiments, the composition is substantially free of Bacteroides bacteria. A composition is substantially free of a bacterial type if that type makes up less than 10% of the bacteria in a composition, preferably less than 5%, even more preferably less than 1%, most preferably less than 0.5%, or even 0% of the bacteria in the composition.

In some embodiments, the composition comprises a fecal sample comprising at least one species of *Akkermansia* (Akk) and at least one species of *Parabacteroides* (Pb). In some embodiments, the fecal sample is from a fecal bank. In some embodiments, the compositions may be added to a fecal sample prior to administration to the subject.

In some embodiments, provided herein are methods of treating or preventing seizures by administering a composition (e.g., a fecal sample) that is enriched for at least one species of *Akkermansia* (Akk) and at least one species of *Parabacteroides* (Pb) to the subject. The fecal sample is enriched if at least 0.01%, at least 0.02%, at least 0.03%, at least 0.04%, at least 0.05%, at least 0.06%, at least 0.07%, at least 0.08%, at least 0.09%, at least .1%, at least 0.2%, at least 0.3%, at least 0.4%, at least 0.5%, at least 0.6%, at least 0.7%, at least 0.8%, at least 0.9%, at least 1%, or at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% of the bacteria in the fecal sample is *Akkermansia* (Akk). In some embodiments, fecal sample is enriched if at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, or at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% of the bacteria in the fecal sample is and *Parabacteroides* (Pb). In some embodiments, the fecal sample is from a fecal bank. In some embodiments, the fecal sample is from a donor.

The composition may further comprise a nutrient. In some embodiments, the nutrient aids in the growth of bacteria (e.g., bacteria disclosed herein). In some embodiments, the nutrient is a lipid (e.g., lineoleic acid, stearic acid, or palmitic acid). In some embodiments, the nutrient may be conjointly administered with a composition disclosed herein. As used herein, the phrase "conjoint administration" refers to any form of administration of two or more different agents (e.g., a composition disclosed herein and a nutrient disclosed herein) such that the second agent is administered while the previously administered agent is still effective in the body. For example, the compositions disclosed herein and the nutrients disclosed herein can be administered either in the same formulation or in a separate formulation, either concomitantly or sequentially.

Actual dosage levels of the active ingredients in the pharmaceutical compositions may be varied to obtain an amount of the active ingredient that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

EXEMPLIFICATION

Example 1: Materials and Methods

Animals and Diets

Three to four week old SPF wild type Swiss Webster mice (Taconic Farms), GF wild type Swiss Webster mice (Taconic Farms) and SPF C3HeB/FeJ KCNA1 KO mice (Jackson Laboratories) were bred in UCLA's Center for Health Sciences Barrier Facility. Breeding animals were fed "breeder" chow (Lab Diets 5K52). Experimental animals were fed standard chow (Lab Diet 5010), 6:1 ketogenic diet (Harlan Teklad TD.07797.PWD) or vitamin- and mineral-matched control diet (Harlan Teklad TD.150300). Juvenile mice were used to i) mimic the typical use of the KD to treat pediatric and adolescent epileptic patients, ii) align the timing of mouse brain development to early human brain development, where neurodevelopmental milestones in 3-week old mice are comparable to those of the 2-3 year old human brain, and iii) preclude pre-weaning dietary treatment, where effects of the diet on maternal behavior and physiology would confound direct effects of the diet on offspring. Mice were randomly assigned to an experimental group. All animal experiments were approved by the UCLA Animal Care and Use Committee.

6-Hz Psychomotor Seizure Assay

The 6-Hz test was conducted as previously described. Pilot studies revealed no sexual dimorphism in seizure threshold. All subsequent experimental cohorts contained male mice. One drop (~50 ul) of 0.5% tetracaine hydrochloride ophthalmic solution was applied to the corneas of each mouse 10-15 min before stimulation. Corneal electrodes were coated with a thin layer of electrode gel (Parker Signagel). A constant-current current device (ECT Unit 57800, Ugo Basile) was used to deliver current at 3 sec duration, 0.2 ms pulse-width and 6 pulses/s frequency. CC50 (the intensity of current required to elicit seizures in 50% of the experimental group) was measured as a metric for seizure susceptibility. Pilot experiments were conducted to identify 24 mA as the CC50 for SPF wild-type Swiss Webster mice. Each mouse was seizure-tested only once, and thus at least n>6 mice were used to adequately power each experiment group. To determine CC50s for each experimental group, 24 mA currents were administered to the first mouse per experimental group per cohort, followed by fixed increases or decreases by 2 mA intervals. Mice were restrained manually during stimulation and then released into a new cage for behavioral observation. Locomotor behavior was recorded using Ethovision XT software (Noldus) and quantitative measures for falling, tail dorsiflexion (Straub tail), forelimb clonus, eye/vibrissae twitching and behavioral remission were scored manually. For each behavioral parameter, we observed no correlation between percentage incidence during 24 mA seizures and microbiota status or group seizure susceptibility, suggesting a primary effect of the microbiota on seizure incidence rather than presentation or form. Latency to exploration (time elapsed from when an experimental mouse is released into the observation cage (after corneal stimulation) to its first lateral movement) was scored using Ethovision and manually with an electronic timer. Within-diet groups were tested blindly. Authentic blinding across different-diet groups was not possible due to diet-induced changes in stool color. However, results from pilot experiments reveal no significant differences between results acquired from the same experimental groups tested blinded vs non-blinded. Mice were scored as protected from seizures if they did not show seizure behavior and resumed normal exploratory behavior within 10 s. Seizure threshold (CC50) was determined as previously described, using the average log interval of current steps per experimental group, where sample n is defined as the subset of animals displaying the less frequent seizure behavior. Data used to calculate CC50 are also displayed as latency to explore for each current intensity, where n represents the total number of biological replicates per group regardless of seizure outcome.

Glucose Measurements

Blood samples were collected by cardiac puncture and spun through SST vacutainers (Becton Dickinson) for serum separation. Glucose levels were detected in sera by colorimetric assay according to the manufacturer's instructions (Cayman Chemical). Data compiled across multiple experiments are expressed as glucose concentrations normalized to SPF controls within each experiment.

Beta-hydroxybutyrate (BHB) Measurements

Blood was collected by cardiac puncture and spun through SST vacutainers (Becton Dickinson) for serum separation. The colon was washed and flushed with PBS to remove lumenal contents. Frontal cortex, hippocampus, hypothalamus and cerebellum were microdissected and livers were harvested and washed in PBS. Tissue samples were sonicated on ice in 10 s intervals at 20 mV in RIPA lysis buffer (Thermo Scientific). BHB levels were detected in sera by colorimetric assay according to the manufacturer's instructions (Cayman Chemical). Data were normalized to total protein content as detected by BCA assay (Thermo Pierce). Data compiled across multiple experiments are expressed as BHB concentrations normalized to SPF controls within each experiment.

16S rDNA Microbiome Profiling

Bacterial genomic DNA was extracted from mouse fecal samples or colonic lumenal contents using the MoBio PowerSoil Kit, where the sample n reflects independent cages containing 3 mice per cage. The library was generated according to methods adapted from prior work. The V4 regions of the 16S rDNA gene were PCR amplified using individually barcoded universal primers and 30 ng of the extracted genomic DNA. The PCR reaction was set up in triplicate, and the PCR product was purified using the Qiaquick PCR purification kit (Qiagen). The purified PCR product was pooled in equal molar concentrations quantified by the Kapa library quantification kit (Kapa Biosystems, KK4824) and sequenced by Laragen, Inc. using the Illumina Mi Seq platform and 2 x 250bp reagent kit for paired-end sequencing. Operational taxonomic units (OTUs) were chosen by open reference OTU picking based on 97% sequence similarity to the Greengenes 13_5 database. Taxonomy assignment and rarefaction were performed using QIIME1.8.0 using 85,134 reads per sample. Metagenomes were inferred from closed reference OTU tables using PICRUSt. Results were filtered to display the top 72 genes relevant to amino acid metabolism.

Microbiota Conventionalization

Fecal samples were freshly collected from adult SPF Swiss Webster mice and homogenized in pre-reduced PBS at 1 ml per pellet. 100 ul of the settled suspension was administered by oral gavage to recipient GF mice. For mock treatment, mice were gavaged with pre-reduced PBS.

Antibiotic Treatment

SPF mice were gavaged with a solution of vancomycin (50 mg/kg), neomycin (100 mg/kg) and metronidazole (100 mg/kg) every 12 hours daily for 7 days, according to methods previously described by Reikvam et al., PloS one (6), 2011. Ampicillin (1 mg/ml) was provided ad libitum in drinking water. For mock treatment, mice were gavaged with normal drinking water every 12 hours daily for 7 days. For Kcna1$^{-/-}$ mice, drinking water was supplemented with vancomycin (500 mg/ml), neomycin (1 mg/ml) and ampicillin (1 mg/ml) for 1 week to preclude the stress of oral gavage in seizure-prone mice.

Gnotobiotic Colonization and Bacterial Enrichment in Antibiotic-Treated Mice

*A. muciniphila* (ATCC BAA845) was cultured under anaerobic conditions in Brain Heart Infusion (BHI) media supplemented with 0.05% hog gastric mucin type III (Sigma Aldrich). *P. merdae* (ATCC 43184) and *P. distasonis* (ATCC 8503) were grown in anaerobic conditions in Reinforced Clostridial Media (RCM). $10^9$ cfu bacteria were suspended in 200 ul pre-reduced PBS and orally gavaged into antibiotic-treated mice or germ-free mice. When co-administered as "*A. muciniphila* and *Parabacteroides* spp.", a ratio of 2:1:1 was used for *A. muciniphila: P. merdae: P. distasonis*. For mock treatment, mice were gavaged with pre-reduced PBS. Pilot studies revealed no significant differences between colonization groups in fecal DNA concentration or 16S rDNA amplification, as measures relevant to bacterial load. Mice were maintained in microisolator cages and handled aseptically. Mice were seizure tested at 14 days after colonization.

Fecal Microbiota Transplant

Fecal samples were freshly collected from donor mice fed KD or CD for 14 days and suspended at 50 mg/ml in pre-reduced PBS. Antibiotic-treated mice were colonized by oral gavage of 100 ul suspension. For mock treatment, mice were gavaged with pre-reduced PBS. Mice were housed in microisolator cages and handled aseptically. Seizure testing was conducted at 4 days after transplant.

Bacterial Treatment

*A. muciniphila, P. merdae* and *P. distasonis* were freshly cultured in anaerobic conditions as described above, and then washed, pelleted and re-suspended at $5 \times 10^9$ cfu/ml in pre-reduced PBS. *A. muciniphila* with *Parabacteroides* spp. were prepared at a 2:1:1 ratio. For heat-killing, bacteria were placed at 95° C. for 10 min. Mice were gavaged every 12 hours for 28 days with 200 ul bacterial suspension or sterile pre-reduced PBS as vehicle control.

Kcna1 Seizure Recordings

EEG Implantation and Recovery

EEGs were recorded from male and female Kcna1$^{-/-}$ mice at 6-7 weeks of age. Kcna1$^{+/+}$ littermates were used as controls. There were no significant differences observed between males and females in seizure frequency and duration. Data presented include both sexes. Mice were anesthetized with isoflurane (5% induction, 2% maintenance) and eye ointment applied to each eye. Fur was removed along the head, and the area was cleaned with three alternative scrubs of chlorohexidine and 70% isopropanol. In a biosafety cabinet, mice were positioned in a stereotaxic apparatus (Harvard Biosciences) and 1 mg/kg lidocaine +1 mg/kg bupivacaine was applied locally along the incision site. Using sterile surgical tools, a 2 cm incision was made along the dorsal midline from the posterior margin of the eyes to a point midway between the scapulae. A subcutaneous pocket along the dorsal flank was created and the pocket irrigated with sterile saline. A wireless telemetry transmitter was inserted with bi-potential leads oriented cranially. The skull was cleaned with 3% hydrogen peroxide followed by 70% isopropanol. Using a 1.0 mm micro drill bit, the skull was perforated to generate two small holes halfway between the bregma and lambda, and 1-2 mm from the sagittal suture. Bilateral EEG recording electrodes (Data Sciences International (DSI) PhysioTel, ETA-F10) were epidurally implanted over the frontoparietal cortex. Sterile acrylic was applied to the dried area. The incision site was closed with absorbable 5-0 sutures and cleaned with 3% hydrogen peroxide followed by 70% ethanol. Animals were housed individually in autoclaved microisolator cages and allowed to recover for 3-5 days before recordings were initiated.

Data Acquisition and Analysis

During EEG recordings, animals were freely moving and maintained on experimental diet. EEG traces were acquired over 3 days using the DSI Ponemah V5.1 data acquisition system. Simultaneous video recordings of behavioral seizures were correlated with EEG recordings and scored based on an adapted Racine scale and defined by 5 stages: 1) myoclonic jerk, 2) head stereotypy and facial clonus, 3) bilateral and alternating forelimb/hindlimb clonus, 4) rearing and falling, and 5) generalized tonic-clonic episodes. Data were analyzed by a blinded researcher using Neuroscore CNS Software (DSI). EEG signals were filtered using a 10 Hz high pass filter, and seizure events were detected by blinded manual scoring. Seizures were defined as patterns of high-frequency, high-voltage synchronized heterogeneous spike wave forms with amplitudes at least 2-fold greater than background with more than 6 s duration. The spike frequency was determined as number of spikes occurring above baseline in a given seizure, and the interspike interval was analyzed as a function of the time between spikes for five representative seizures in each phase per mouse. The duration of maximum spike amplitude was determined as the percent time spent in spikes that were three times as large as the baseline for five representative seizures in each phase per mouse.

Colonic Lumenal and Serum Metabolomics

Samples were collected from mice housed across independent cages, with at least 2 mice per cage. Colonic lumenal contents were collected from terminal mouse dissections, immediately snap frozen in liquid nitrogen and stored at −80° C. Serum samples were collected by cardiac puncture, separated using SST vacutainer tubes and frozen at −80° C. Samples were prepared using the automated Micro-Lab STAR system (Hamilton Company) and analyzed on GC/MS, LC/MS and LC/MS/MS platforms by Metabolon, Inc. Protein fractions were removed by serial extractions with organic aqueous solvents, concentrated using a TurboVap system (Zymark) and vacuum dried. For LC/MS and LC-MS/MS, samples were reconstituted in acidic or basic LC-compatible solvents containing >11 injection standards and run on a Waters ACQUITY UPLC and Thermo-Finnigan LTQ mass spectrometer, with a linear ion-trap front-end and a Fourier transform ion cyclotron resonance mass spectrometer back-end. For GC/MS, samples were derivatized under dried nitrogen using bistrimethyl-silyl-trifluoroacetamide and analyzed on a Thermo-Finnigan Trace DSQ fast-scanning single-quadrupole mass spectrometer using electron impact ionization. Chemical entities were identified by comparison to metabolomic library entries of purified standards. Following log transformation and imputation with minimum observed values for each compound, data were analyzed using one-way ANOVA to test for group effects. P and q-values were calculated based on two-way ANOVA contrasts. Principal components analysis was used to visualize variance distributions. Supervised Random Forest analysis was conducted to identify metabolomics prediction accuracies.

Hippocampal Metabolomics

Hippocampal tissues were homogenized in 1 ml cold 80% MeOH and vigorously mixed on ice followed by centrifugation ($1.3*10^4$ rpm, 4° C.). 5 ug supernatant was transferred into a glass vial, supplemented with 5 nmol D/L-norvaline, dried down under vacuum, and finally re-suspended in 70% acetonitrile. For the mass spectrometry-based analysis of the sample, 5 l were injected onto a Luna NH2 (150 mm×2 mm, Phenomenex) column. The samples were analyzed with an UltiMate 3000RSLC (Thermo Scientific) coupled to a Q Exactive mass spectrometer (Thermo Scientific). The Q Exactive was run with polarity switching (+4.00 kV/−4.00 kV) in full scan mode with an m/z range of 70-1050. Separation was achieved using A) 5 mM NH4AcO (pH 9.9) and B) ACN. The gradient started with 15% A) going to 90% A) over 18 min, followed by an isocratic step for 9 min. and reversal to the initial 15% A) for 7 min. Metabolites were quantified with TraceFinder 3.3 using accurate mass measurements (≤3 ppm), retention times of pure standards and MS2 fragmentation patterns. Data analysis, including principal component analysis and hierarchical clustering was performed using R.

Amino Acid Supplementation

Four-week old Swiss Webster SPF mice were treated with antibiotics, colonized with *A. muciniphila* and *Parabacteroides* spp., and fed KD for 14 days, as described in methods above. Beginning on the evening of day 11, mice were injected intraperitoneally every 12 hours for 3 days with ketogenic amino acid cocktail (Sigma Aldrich)-L-leucine (2.0 mg/kg), L-lysine (2.0 mg/kg), L-tyrosine (2.4 mg/kg), L-tryptophan (1.6 mg/kg), and L-threonine (3.1 mg/kg) in sterile PBS. Concentrations are based on physiological levels reported for each amino acid in mouse blood, and on fold-changes observed in our metabolomics dataset for each amino acid between control SPF CD and AkkPb KD mice. Vehicle-treated mice were injected with PBS (200 ul/30 g mouse). On day 14, mice were tested for 6-Hz seizures 2 hours after the final morning amino acid injection, with a prior 1-hour acclimation period in the behavioral testing room.

GGsTop Treatment

For wild type mice: 4-week old SPF Swiss Webster mice were fed CD ad libitum for 14 days. Beginning on the evening of day 11, mice were orally gavaged every 12 hours with 13.3 mg/kg 3-[[(3-amino-3 -carboxypropyl)methoxyphosphinyl]oxy]benzeneacetic acid (GGsTop, Tocris Bioscience) in sterile water. Vehicle-treated mice were gavaged with sterile water (200 ul/30 g mouse). On day 14, mice were tested for 6-Hz seizures 2 hours after the final morning GGsTop gavage, with a prior 1-hour acclimation period in the behavioral testing room. For Kcna1 mice: 3-4 week old Kcna1$^{−/−}$ mice were fed the CD ad libitum for 23 days. On Day 15, EEG transmitters were implanted as described in the Kcna1 Seizure Recordings section above. On the evening of day 18, mice were orally gavaged every 12 hours with 13.3 mg/kg GGsTop through the morning of day 21. Seizures were recorded over 3 days by EEG beginning 2 hours after the final gavage.

Cross-Feeding in vitro Assay

Cross-feeding was measured as previously described. *A. muciniphila* was embedded at $2\times10^6$ cfu/ml in 5 ml pre-reduced CD or KD-based liquid media supplemented with 1% agar at the bottom of an anaerobic tube, and *P. merdae* was overlaid above it at $6\times10^6$ cfu/ml in 5 ml pre-reduced M9 minimal media. Diet-based media were generated by aseptically suspending mouse KD vs. CD diets, described above, to 2 kcal/ml in M9 media. Pilot experiments confirmed no ectopic translocation of embedded *A. muciniphila* from the agar compartment into the above M9 liquid compartment. For each time point, aliquots were taken from the top and bottom compartments, plated in a dilution series in rich media (RCM for *P. merdae* and BHI +0.05% mucins for *A. muciniphila*), and colonies were counted. For GGsTop pre-treatment experiments, *P. merdae* was incubated with 500 uM GGsTop vs vehicle in RCM media at 37° C. for 2 hours and then washed with sterile media. Pilot experiments revealed no significant effect of GGsTop pre-treatment on *P. merdae* viability.

GGT Activity Assay

GGT activity was measured as previously described. For anaerobic cultures, bacteria were seeded at $3 \times 10^5$ cfu/ml in CD- and KD-based media. 1 ml bacterial suspension was pelleted and frozen at −80° C. for 1 hr. Separate aliquots of the same suspension were plated in BHI mucin agar media or RCM and incubated at 37° C. in a Coy anaerobic chamber for later data normalization by bacterial cfu. Pellets were then resuspended in 250 ul lysis buffer (50 mM Tris-HCl with 1 ug/ml lysozyme) and incubated on ice for 30 min. For fecal samples, one pellet was weighed and homogenized in 1 ml lysis buffer. Bacterial and fecal suspensions were then sonicated (QSonica 125) and centrifuged at 12000×g for 10 min at 4° C. 20 ul supernatant was mixed with 180 ul substrate buffer (2.9 mM L-gamma-glutamyl-3-carboxy-4-nitroanilide (Gold Bio), 100 mM of glycylglycine (Sigma Aldrich), 100 mM Tris-HCl), and 500 uM GGsTop (if noted). Absorbance at 405 nm denoting production of 3-carboxy-4-nitroaniline was measured every minute for 1 hr at 37° C. using an automated multimode plate reader (Biotek Synergy H1).

Intestinal Permeability Assay

Mice were fasted for 4 hr beginning at 7 am before gavage with 0.6 g/kg 4 kDa FITC-dextran (Sigma Aldrich). 4 hours after gavage, serum samples were collected by cardiac puncture, diluted 3-fold in water and read in duplicate for fluorescence intensity at 521 nm using a Synergy H9 multimode plate reader (Biotek) against a standard dilution series of stock FITC-dextran in 3-fold diluted normal mouse serum in water.

Statistical Analysis

Statistical analysis was performed using Prism software (GraphPad). Data were assessed for normal distribution and plotted in the figures as mean±s.e.m. For each figure, n=the number of independent biological replicates. No samples or animals were excluded from the analyses. Differences between two treatment groups were assessed using two-tailed, unpaired Student's t test with Welch's correction. Differences among >2 groups with only one variable were assessed using one-way ANOVA with Bonferroni post hoc test. Data for Kcna1 mice were analyzed by non-parametric one-way ANOVA with Dunn's post hoc test. Two-way ANOVA with Bonferroni post-hoc test was used for ≥2 groups with two variables (e.g. seizure time course, BHB time course, metabolomics data, bacterial growth curves). One-way ANOVA with repeated measures and Bonferroni post-hoc test was used for GGT assays. Significant differences emerging from the above tests are indicated in the figures by *$P<0.05$, $P<0.01$, *$P<0.001$, ****$P<0.0001$ Notable near-significant differences ($0.5<P<0.1$) are indicated in the figures. Notable non-significant (and non-near significant) differences are indicated in the figures by "n.s."

The materials and methods described in this example were used for carrying out the experiments described in Examples 2 and 3.

Example 2: Bacterial Gamma-Glutamylation Impacts Seizure Susceptibility

Figure 1A:
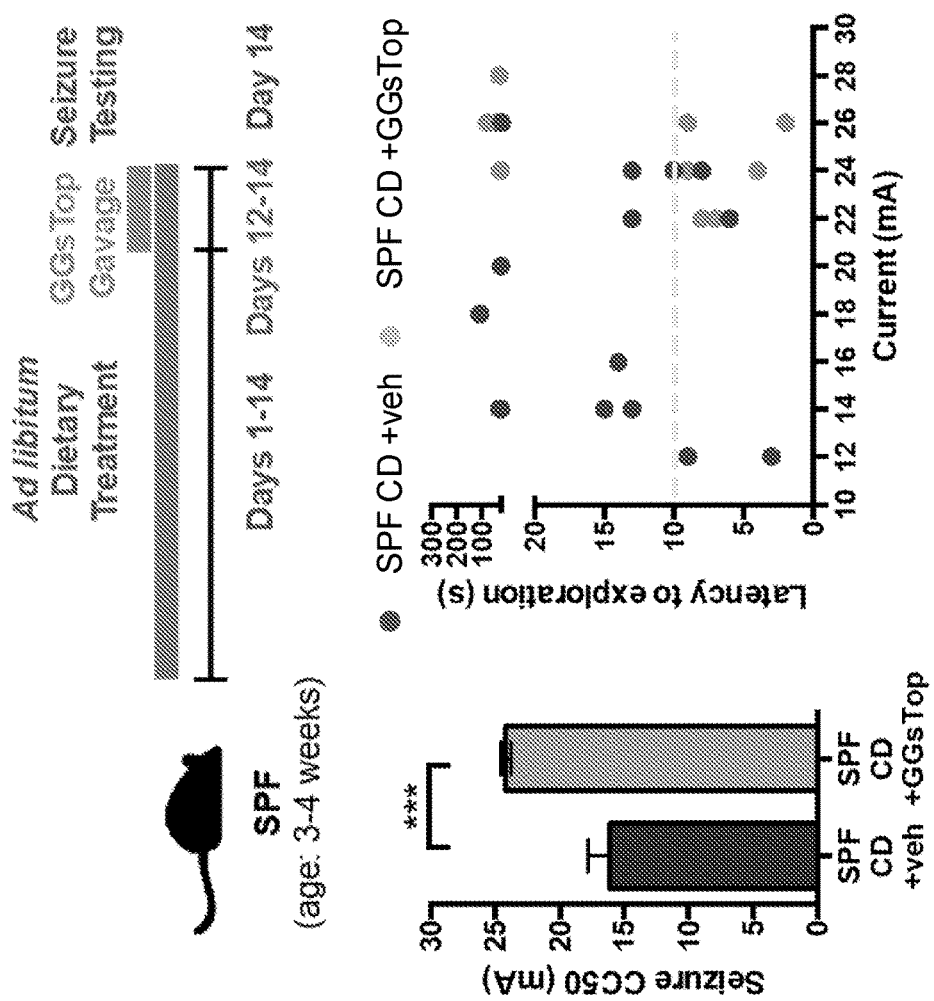
FIGS. 1A through 1D show reduction of gamma-glutamyltranspeptidase activity and subsequent seizure protection.
Figure 1B:
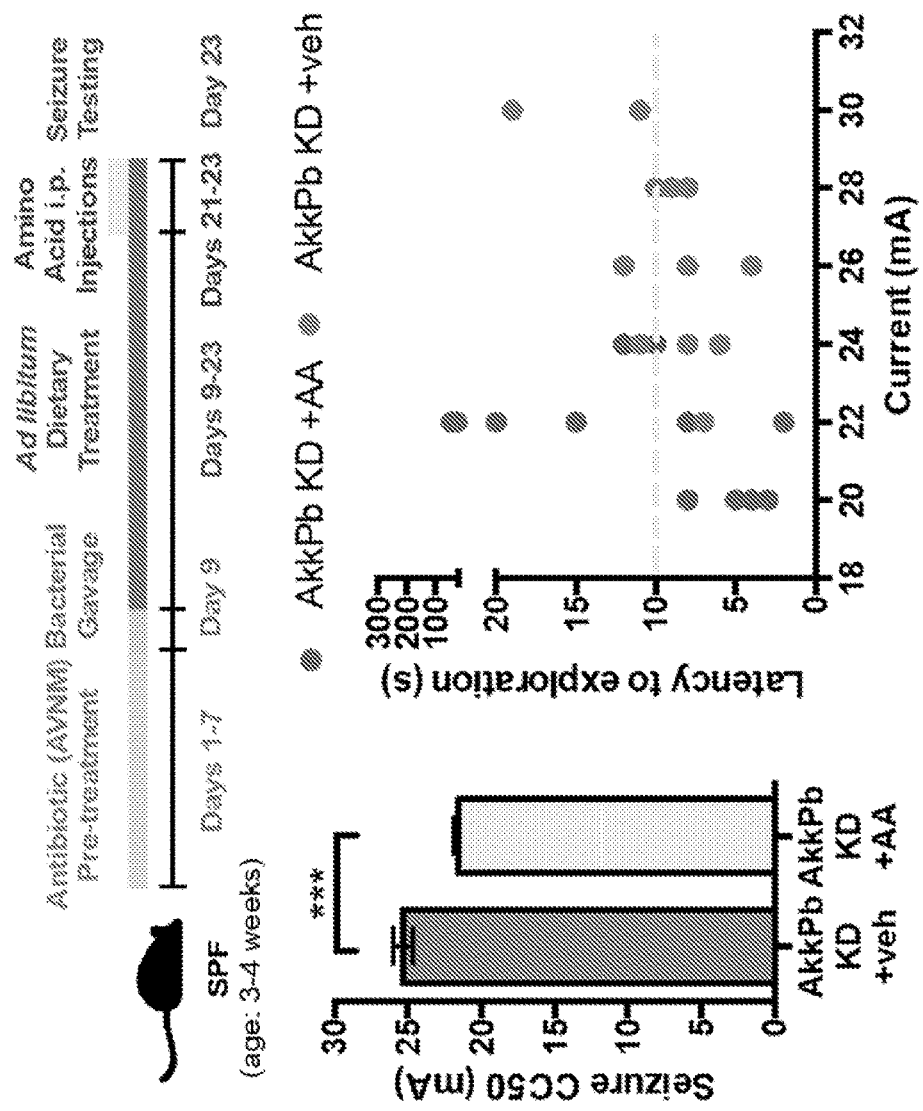

Based on previous data demonstrating that essential ketogenic gamma glutamyl-amino acids are reduced in colonic lumen and serum of seizure-protected versus seizure-susceptible experimental groups, it is possible that microbiota-dependent restriction of ketogenic GG-amino acids is important for mediating the anti-seizure effects of the ketogenic diet. Gamma-glutamylated forms of amino acids are generated by transpeptidation of gamma-glutamyl moieties from glutathione onto amino acids. To determine whether gamma-glutamylation of amino acids impacts seizure susceptibility, SPF CD mice were gavaged for 3 days with GGsTop, a selective irreversible inhibitor of GGT. SPF CD mice treated with GGsTop exhibited increases in seizure thresholds toward levels seen in SPF KD mice (FIG. 1A). Similarly, EEG recordings of CD-fed SPF Kcna1−/− mice treated with GGsTop displayed a significant decrease in seizures per day (FIG. 2). This demonstrated that peripheral inhibition of gamma-glutamylation and restriction of GG-amino acids promoted seizure protection, consistent with observed metabolomic decreases of ketogenic GG-amino acids in colonic lumenal content and sera from seizure-protected groups compared to seizure-susceptible controls. Importantly, to determine whether restriction of amino acids, rather than catabolism of glutathione, was necessary for the anti-seizure effects of the KD microbiota, KD-fed *A. muciniphila* and *Parabacteroides* spp.-enriched mice were supplemented by bi-daily intraperitoneal injection for 3 days with combined leucine, lysine, threonine, tryptophan and tyrosine, and then tested for 6-Hz seizures. Physiologically-relevant concentrations of amino acids were calculated based on serum metabolomic data, such that dosages for each were projected to restore blood levels to that seen in vehicle-treated SPF CD controls. Elevating systemic levels of ketogenic amino acids decreased seizure thresholds to levels seen in vehicle-treated SPF CD controls (FIG. 1B). This suggested that restriction of peripheral ketogenic amino acids is necessary for mediating microbiota- and KD-dependent increases in seizure resistance.

Figure 1C:
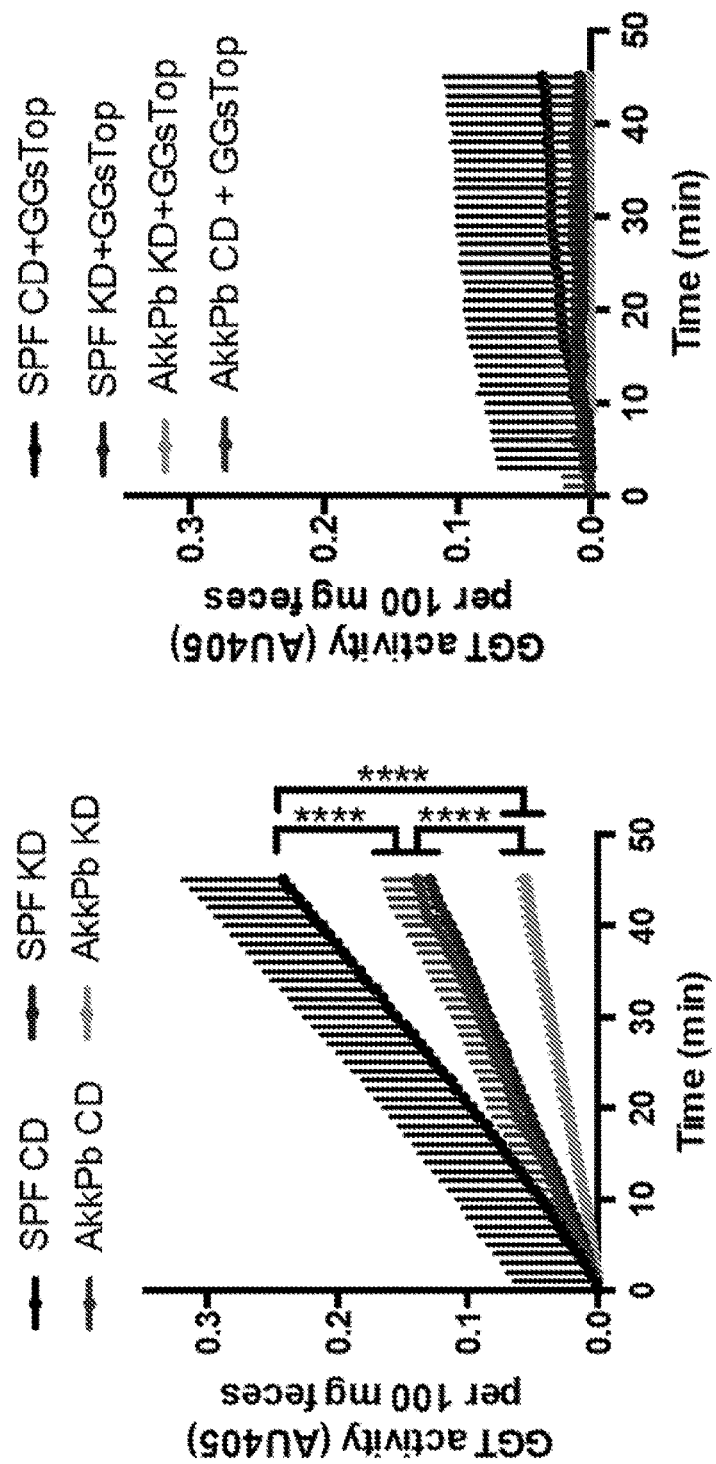
Figure 1D:
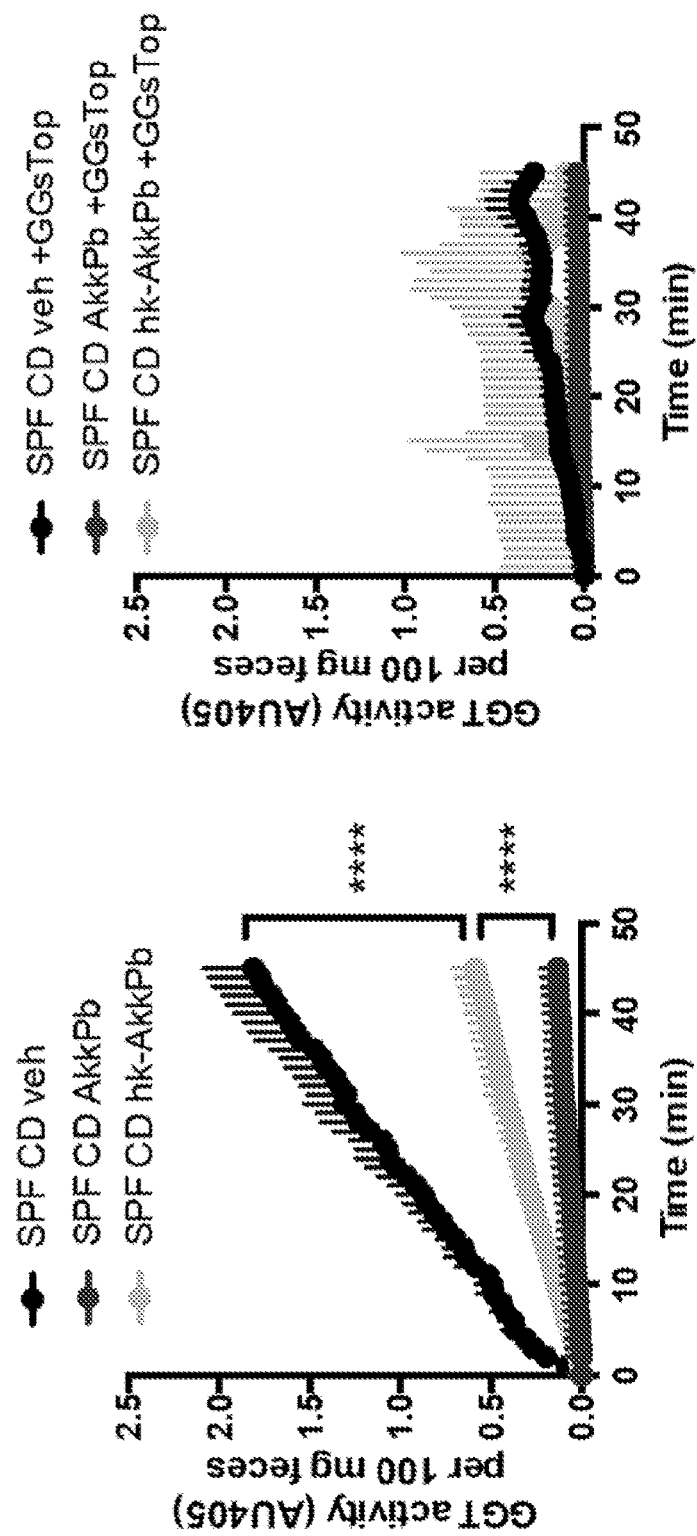

Both host cells and particular bacterial species exhibit GGT activity. To gain insight into whether the KD and interactions between *A. muciniphila* and *Parabacteroides* spp. suppressed bacterial gamma-glutamylation in vivo, GGT activity in fecal samples collected from SPF or *A. muciniphila* and *Parabacteroides* spp.-enriched mice fed the CD or KD were measured. Feeding SPF mice with KD decreased fecal GGT activity compared to CD controls (FIG. 1C). Similar reduction in fecal GGT activity was seen after enriching *A. muciniphila* and *Parabacteroides* spp. in CD-fed mice. Moreover, enriching *A. muciniphila* and *Parabacteroides* spp. and feeding with KD further decreased fecal GGT activity relative to that seen in SPF KD and SPF CD mice. Exposing all fecal samples to the GGT inhibitor GGsTop eliminated the detected signals, confirming that the measurements reflected GGT activity. Consistent with this, treatment of CD-fed SPF mice with *A. muciniphila* and *Parabacteroides* spp. decreased fecal GGT activity relative to vehicle-treated controls and mice treated with heat-killed bacteria (FIG. 1D). Overall, these data revealed that enriching for or exogenous treatment with *A. muciniphila* and *Parabacteroides* spp. reduced fecal GGT activity, which could explain the low levels of colonic and serum GG-amino acids observed in seizure-protected mice.

Example 3: Bacterial Gamma-Glutamylation is affected by A. muciniphila and Parabacteroides spp. Interaction To explore whether bacterial gamma-glutamylation was affected by interactions between A. muciniphila and Parabacteroides spp., GGT activity in bacteria grown in an in vitro cross-feeding system was measured. Since A. muciniphila does not exhibit GGT activity, the focus was particularly on P. merdae, where GGT activity was ablated by GGsTop (FIG. 3A). When A. muciniphila was embedded in a CD- or KD-based agar, and P. merdae was overlaid in M9 minimal media over the agar, both bacteria exhibited enhanced growth (FIG. 3B and FIG. 3C), which suggested that A. muciniphila liberated soluble factors to enable P. merdae growth and in turn P. merdae enhanced A. muciniphila growth. Pilot experiments revealed no growth of A. muciniphila in M9 media when overlaid on P. merdae embedded in KD or CD agar, which suggested that A. muciniphila could not rely solely on cross-feeding from P. merdae to persist. Interestingly, P. merdae exhibited high GGT activity that was eliminated by the addition of A. muciniphila embedded in CD or KD agar (FIG. 3D and FIG. 3E). To determine whether reduction of GGT activity in P. merdae promoted A. muciniphila growth, P. merdae was pre-treated with vehicle or GGsTop to pharmacologically inhibit GGT activity prior to testing in the cross-feeding assay. A. muciniphila exposed to P. merdae that was pre-treated with GGsTop exhibited increased growth at 24 hours after incubation as compared to A. muciniphila exposed to vehicle-treated P. merdae (FIG. 4). Taken together, these findings suggested that A. muciniphila was capable of metabolizing components from the KD and CD diet to support P. merdae growth, and that this cooperative interaction reduced GGT activity. In turn, reductions in GGT activity in P. merdae promoted A. muciniphila growth. This was consistent with the finding that enrichment of A. muciniphila and Parabacteroides spp. reduced fecal GGT activity, colonic lumenal GG-amino acids and serum GG-amino acids.

As demonstrated in the Examples, amino acid restriction is required for seizure protection and that inhibition of GGT promotes seizure protection. This aligns with previous studies that linked GGT activity to altered seizure severity. In a study of 75 epileptic patients, high serum GGT activity was observed in 84.5% of the patients compared to controls. In a rat seizure model, GGT activity was increased after 5 consecutive daily electroshock deliveries. Decreases in various peripheral amino acids are associated with KD-mediated seizure suppression in animals and humans. Based on the data herein and existing literature on roles for peripheral amino acids as substrates for brain neurotransmitter biosynthesis, it is possible that bacterial regulation of GG-amino acids alters brain import of amino acids that fuel GABA/glutamate metabolism (FIG. 5). Notably, several gut bacteria are reported to synthesize GABA de novo; however, circulating GABA exhibits limited transport across the blood-brain barrier. In addition, changes in the gut microbiota have been associated with alterations in brain GABA levels, but the molecular mechanisms involved remained unclear. Additional studies are needed to determine whether GG-amino acids influence brain transport of amino acids and local synthesis of glutamate versus GABA.

Random forests/machine-learning analyses revealed the most discriminatory biomarkers in feces (FIG. 6-FIG. 8) and serum (FIG. 9-FIG. 11) in animals treated with antibiotics versus animals not treated with antibiotics (FIG. 6 and FIG. 9), in animals fed a control diet versus animals fed a ketogenic diet (FIG. 7 and FIG. 10), and in seizure-protected animals versus seizure-susceptible animals (FIG. 8 and FIG. 11). The corresponding box plots of the most discriminatory biomarkers from each subset are found in FIG. 12-FIG. 17.

Overall, the present disclosure demonstrates a novel role for select KD-associated gut bacteria—A. muciniphila and Parabacteroides spp.—in mediating and conferring seizure protection in mouse models for refractory epilepsy. Increases in A. muciniphila were similarly observed during fasting in humans, hamsters, squirrels, and pythons and in response to caloric restriction and high polyunsaturated fat diets in mice. A. muciniphila and Parabacteroides spp. are also positively associated with increased ketosis and the ketogenic diet in humans. This data reveals a likely pathway whereby the KD promotes select microbe-microbe interactions that reduce host levels of ketogenic GG-amino acids and elevates the total bioavailability of GABA relative to glutamate in the hippocampus. Pharmacological inhibition of gamma-glutamylation increased seizure thresholds, which suggested that reduced GGT activity was important for mediating the anti-seizure effects of the KD-associated gut microbiota in mice. Notably, given that the lack of bacterial GGT activity in the GF condition is associated with seizure susceptibility, it is likely that A. muciniphila and Parabacteroides spp. contribute functions in addition to suppression of GGT activity that may also contribute to seizure protection.

Example 4: Selecting a Subject Afflicted with a Seizure Disorder

In a biological sample (e.g., serum sample, fecal sample) from a subject, which either is obtained from the subject or is provided after having been obtained from the subject, a metric of at least one biomarker associated with a seizure disorder is detected. The metric is the presence, absence, amount, or activity of the at least one biomarker. The biomarkers can be detected or assessed (e.g., directly, through their reaction intermediates, through their reaction products, through their coupled reaction constituents) via various methods, such as ultraviolet-visible spectroscopy, mass spectrometry, nuclear magnetic resonance, high performance liquid chromatography, electrophoresis, immunoassays, fluorescence spectroscopy, radiography, colorimetry, calorimetry, circular dichroism, or any other known technique.

Once such a biomarker's metric is determined, it is compared to the same metric for the same biomarker in a reference sample representative of a subject that does not have the seizure disorder (e.g., a reference sample that has been obtained from a subject without the seizure disorder, a reference sample that has been obtained from a subject without any seizure disorder). As an example, if the metric is serum concentration and the biomarker is cysteine, the cysteine concentration in a serum sample of the subject is compared to the cysteine concentration in a reference serum sample.

Once it is determined that the metric in the biological sample differs from that in the reference sample, the subject from whom the biological sample had originated is selected (e.g., identified as being a subject that is afflicted with a seizure disorder). The determination of whether the metrics differ from each other can be made based on whether the biomarker is present in one sample while being absent in the other one, or on whether the measurement in one sample differs by more than a threshold (e.g., 20%, 30%, 40%, 50%, 60%, 70%, 80%, 90%) as compared to the measurement in the other sample. In some experiments, the direction of the difference can also be considered in accord with the disclosures of FIGS. 6 through 17 (e.g., a subject is selected if the biological sample has a lower-than-reference amount of one of the biomarkers labelled with an asterisk in FIG. 8, a subject is selected if the biological sample has a higher-than-reference amount of one of the biomarkers not labelled with an asterisk in FIG. 8, a subject is selected if the biological sample has a lower-than-reference amount of one of the biomarkers labelled with an asterisk in FIG. 7, a subject is selected if the biological sample has a higher-than-reference amount of one of the biomarkers not labelled with an asterisk in FIG. 7, a subject is selected if the biological sample has a higher-than-reference amount of one of the biomarkers labelled with an asterisk in FIG. 6, a subject is selected if the biological sample has a lower-than-reference amount of one of the biomarkers not labelled with an asterisk in FIG. 6).

Example 5: Treating a Subject Afflicted with a Seizure Disorder

A subject afflicted with a seizure disorder is selected, in whom a metric (e.g., presence, absence, amount, activity) of at least one biomarker (e.g., a biomarker listed in FIGS. 6 through 17) associated with a seizure disorder (e.g., refractory epilepsy, non-refractory epilepsy, autism spectrum disorder, Rett syndrome, fragile X, attention deficit disorder, or attention-deficit/hyperactivity disorder) differs (e.g., is present vs. absent, is absent vs. present, is less by at least 20%, is more by at least 20%) from the same metric of the same biomarker in a reference sample representative of a subject without the seizure disorder (e.g., same seizure disorder, any seizure disorder). Once such a subject is selected, an effective amount of a pharmaceutical composition is administered to the subject afflicted with the seizure disorder to treat that seizure disorder. As an example, the pharmaceutical composition can include bacteria of the *Akkermansia* (Akk) and *Parabacteroides* (Pb) genera (e.g., collectively—or individually for either—at a percentage of 10, 20, 30, 40, 50, 60, 70, 80, or 90 out of the total bacterial content of the pharmaceutical composition, for example in terms of colony forming units). The administration can be carried out once, or once per a period (e.g., day). The pharmaceutical composition can be in pill form, and can be administered orally. After the administration, the metric of the at least one biomarker in a biological sample from the subject differs less from that in the reference sample as compared to the pre-administration metric. After the administration, the seizure disorder is either ameliorated or treated.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating a subject afflicted with a seizure disorder, the method comprising
   (a) selecting a subject afflicted with a seizure disorder in whom presence, absence, amount, or activity of at least one biomarker associated with a seizure disorder differs from presence, absence, amount, or activity of the same biomarker in a reference sample representative of a subject without the seizure disorder; and
   (b) administering to the subject afflicted with the seizure disorder an effective amount of a pharmaceutical composition to treat the seizure disorder,
   wherein the pharmaceutical composition comprises bacteria of the *Akkermansia* (Akk) and *Parabacteroides* (Pb) genera; and
   wherein each of the at least one biomarkers is selected from GABA/glutamate ratio, glutamine, leucine, lysine, threonine, tryptophan, tyrosine, gamma-glutamyl (GG)-leucine, gamma-glutamyl (GG)-lysine, gamma-glutamyl (GG)-threonine, gamma-glutamyl (GG)-tryptophan, gamma-glutamyl (GG)-tyrosine, arabonate, xylonate, N-acetylmethionine, myristoleoylcarnitine (C14:1), cytidine 5'-monophosphate (5'-CMP), 1-palmitoly-2- linoleoyldigalactosylg, riboflavin (Vitamin B2), ursocholate, isovalerate, glucoronate, creatine, 1-palmitoyl-GPI (16:0), pipecolate, campesterol, laurylcarnitine (C12), glucose, ethylmalonate, delta-tocopherol, palmitoylcarnithine (C16), picolinate, 6-oxolithocholate, cysteine, 2-oxoarginine, N6-formyllysine, ribulose/xylulose, 3-ureidopropionate, 3-methylcytidine, N6-carboxymethyllysine, N-formylphenylalanine, 3-methyl-2-oxobutyrate, 4-guanidinobutanoate, p-cresol sulfate, imidazole propionate, phenylacetylglycine, perfluorooctanesulfonic acid (PFOS), ergothioneine, indolepropionate, tauro-beta-muricholate, p-cresol-glucoronide, cholate, indoleacrylate, 1-palmitoleoglycerol (16:1), cystathionine, 3-methylglutaconate, palmitoleate (16:1 n7), sphingomyelin (d18:1/25:0 d19:0/24:1 d20:1/23:0 d19:1/24:0), decanoylcarnitine (C10), 17-methylstearate, 1- palmitoleoyl-GPC (16:1), stearoyl sphingomyelin (d18:1/18: 0), 4-hydroxyhippurate, N6-carboxymethyllysine, valylleucine, 1-palmitoyl-2-oleoyl-GPI (16:0/18:1), valerylcarnitine (C5), indoleacetylglycine, octanoyl-carnitine (C8), 1-methylnicotinamide, ursodeoxycholate, gamma-glutamyl-epsilon-lysine, 7-ketodeoxycholate, 3-(4-hydroxyphenyl) propionate, 1-palmitoyl-2-oleoyl-GPG (16:0/18:1), dihydrobiopterin, glycerophosphoglycerol, urea, linoleoylcarnitine (C 18:2), palmitoylcholine, 1-stearoyl-GPC (18:0), 2-hydroxyglutarate, indoleacetate, 3-sulfo-L-alanine, glutarate (pentanedioate), p-aminobenzoate (PABA), maltose, stearoylcholine, erythronate, maltotriose, spermine, gamma-glutamyltyrosine, N-formylmethionine, mevalonate, gamma-glutamylhistidine, 3-sulfo-L-alanine, mannitol/sorbitol, gamma-glutamyltryptophan, 1-methylguanidine, homostachydrine, palmitoyl dihydrosphingomyelin (d18:0/16:0), N-trimethyl 5-aminovalerate, sphingomyelin (d18:0/18:0 d19:0/17: 0), homoarginine, pyridoxate, behenoyl dihydrosphingomyelin (d18:0/22:0), 10-undecenoate (11:1n1), betaine, sphingomyelin (d18:1/19:0 d19:1/18:0), sphingomyelin (d18:1/18:1 d18:2/18:0), choline, 2-palmitoleoyl-GPC (16:1), dihomo-linoleoylcarnitine (C20:2), glycosyl-N-stearoyl-sphingosine, stearoylcarnitine (C18), 1-stearoyl-2-linoleoyl-GPC (18:0/18:2), 1-palmitoyl-2-linoleoyl-GPI (16:0/18:2), 2,3-dihyroxy-2-methylbutyrate, 3-methyl-2-oxobutyrate, N-behenoyl-sphingadienine (d18:2/22:0), pyroglutamine, taurocyamine, phenol sulfate, 1-stearoyl-2-oleoyl-GPC (18:0/18:1), dihomo-linolenoylcarnitine, or xanthurenate.

2. The method of claim 1, wherein the subject is human.

3. The method of claim 1, wherein the subject has a neurodevelopmental condition.

4. The method of claim 3, wherein the neurodevelopmental condition is selected from epilepsy, autism spectrum disorder, Rett syndrome, attention deficit disorder, fragile X syndrome, Alzheimer's disease, Huntington's disease, Parkinson's disease, amyotrophic lateral sclerosis (ALS), cancer, stroke, a metabolic disease, a mitochondrial disorder, depression, migraines, and traumatic brain injury (TBI).

5. The method of claim 1, wherein the biomarker is leucine, lysine, threonine, tryptophan, or tyrosine.

6. The method of claim 1, wherein the biomarker is gamma-glutamyl (GG)-leucine, gamma-glutamyl (GG)-lysine, gamma-glutamyl (GG)-threonine, gamma-glutamyl (GG)-tryptophan, or gamma-glutamyl (GG)-tyrosine.

7. The method of claim 1, wherein the biomarker is arabonate/xylonate, N-acetylmethionine, myristoleoylcarnitine (C14:1), cytidine 5'-monophosphate (5'-CMP), 1-palmitoly-2-linoleoyldigalactosylg, riboflavin (Vitamin B2), ursocholate, isovalerate, glucoronate, creatine, 1-palmitoyl-GPI (16:0), pipecolate, campesterol, laurylcarnitine (C12), glucose, ethylmalonate, delta-tocopherol, palmitoylcarnithine (C16), picolinate, 6-oxolithocholate, cysteine, 2-oxoarginine, N6-formyllysine, ribulose/xylulose, 3-ureidopropionate, 3-methylcytidine, N6-carboxymethyllysine, N-formylphenylalanine, 3-methyl-2-oxobutyrate, 4-guanidinobutanoate, p-cresol sulfate, imidazole propionate, phenylacetylglycine, perfluorooctanesulfonic acid (PFOS), ergothioneine, indolepropionate, tauro-beta-muricholate, p-cresol-glucoronide, cholate, indoleacrylate, 1-palmitoleoglycerol (16:1), cystathionine, 3-methylglutaconate, palmitoleate (16:1n7), sphingomyelin (d18:1/25:0 d19:0/24:1 d20:1/23:0 d19:1/24:0), decanoylcarnitine (C10), 17-methylstearate, 1-palmitoleoyl-GPC (16:1), stearoyl sphingomyelin (d18:1/18:0), 4-hydroxyhippurate, N6-carboxymethyllysine, valylleucine, 1-palmitoyl-2-oleoyl-GPI (16:0/18:1), lysine, valerylcarnitine (C5), indoleacetylglycine, or tyrosine.

8. The method of claim 1, wherein the biomarker is octanoylcarnitine (C8), 1-methylnicotinamide, ursodeoxycholate, gamma-glutamyl-epsilon-lysine, 7-ketodeoxycholate, 3-(4-hydroxyphenyl) propionate, 1-palmitoyl-2-oleoyl-GPG (16:0/18:1), dihydrobiopterin, glycerophosphoglycerol, urea, linoleoylcarnitine (C18:2), palmitoylcholine, 1-stearoyl-GPC (18:0), 2-hydroxyglutarate, indoleacetate, 3-sulfo-L-alanine, glutarate (pentanedioate), p-aminobenzoate (PABA), maltose, stearoylcholine, erythronate, maltotriose, spermine, gamma-glutamyltyrosine, N-formylmethionine, mevalonate, gamma-glutamylhistidine, 3-sulfo-L-alanine, mannitol/sorbitol, gamma-glutamyltryptophan, 1-methylguanidine, homostachydrine, palmitoyl dihydrosphingomyelin (d18:0/16:0), N-trimethyl 5-aminovalerate, sphingomyelin (d18:0/18:0 d19:0/17:0), homoarginine, pyridoxate, behenoyl dihydrosphingomyelin (d18:0/22:0), 10-undecenoate (11:1n1), betaine, sphingomyelin (d18:1/19:0 d19:1/18:0), sphingomyelin (d18:1/18:1 d18:2/18:0), choline, 2-palmitoleoyl-GPC (16:1), dihomo- linoleoylcarnitine (C20:2), glycosyl-N-stearoyl-sphingosine, stearoylcarnitine (C18), 1-stearoyl-2- linoleoyl-GPC (18:0/18:2), 1-palmitoyl-2-linoleoyl-GPI (16:0/18:2), 2,3-dihyroxy-2-methylbutyrate, 3-methyl-2-oxobutyrate, N-behenoyl-sphingadienine (d18:2/22:0), pyroglutamine, taurocyamine, phenol sulfate, 1-stearoyl-2-oleoyl-GPC (18:0/18:1), dihomo-linolenoylcarnitine, or xanthurenate.

9. The method of claim 1, wherein the amounts of arabonate/xylonate, N-acetylmethionine, myristoleoylcarnitine (C14:1), riboflavin (Vitamin B2), glucoronate, creatinine, octanoylcarnitine, 1-methylnicotinamide, gamma-glutamyl-epsilon-lysine, dihydrobiopterin, urea, taurocholenate sulfate, laurylcarnitine (C12), creatine, bilirubin (Z Z), and myristoylcarnitine (C14) are increased in the subject.

10. The method of claim 1, wherein the amounts of 1-palmitoyl-GPI (16:0), campesterol, laurylcarnitine (C12), delta-tocopherol, palmitoylcarnitine (C16), linoleoycarnitine (C18:2), palmitoylcholine, 1-stearoyl-GPC (18:0), stearoylcholine, diglycerol, stimasterol, 2-stearoylcholine, stigmasterol, 2-stearoyl-GPE (18:0), myristoylcarnitine (C14), oleoylcarnitine (C18:1) and stearoylcarnitine are increased in the subject.

11. The method of claim 1, wherein the amounts of 3-ureidopropionate, 3-methylcytidine, mevalonate, diglycerol, and lignoceroylcarnitine (C24) are increased in the subject.

12. The method of claim 1, wherein the amounts of PFOS, ergothionneinem tauro-bea-muricholate, 1-methylgunaidinem homostachydrine, palymitoyl dihydrosphingomyelin, sphingomyelin, pyridoxate, riboflavin (Vitamin B2), behenoyl dihyrdrosphingomyelin (d18:0/22:0), 10-undecenoate (11:1n1), tartrate, sphingomyelin (d18:0/20:0 d16:0/22:0), N-stearolytaurine, sphingomyelin (d18:1/17:0 d17:1/18:0 d19:1/16:0), O-sulfo-L- tyrosine, sphingomyelin (d18/1/19:0 d19:1/8:0), cysteine s-sulfate, and sphingomyelin (d18: 2/18:1) are increased in a subject.

13. The method of claim 1, wherein the amounts of 3-methylglutaconate, ribulose/xylulose, decanoylcarnitine (C10), stearoyl sphingomyelin (d18:1/18:0), betaine, sphingomyelin (d18:1/19:0 d18:1/18:0), sphingomyelin (d18:1/18:1 d18:2/18:0), choline, dihomo-linoleoylcarnitine (C20:2), gylosyl-N-stearoyl-shpngosine, palmitoyl dihyrdosphingomyelin, stearoylcarnitine (C18), 1-stearoyl-2-linoleoyl-GPC (18:0/18:2), N-acetyl-1-methylhistidine, palmitoyl sphingomyelin (d18:1/16:0), sphingomyelin (d18: 2/24:2), cis-4-decenolycarnitine (C10:1), oleoycarnitine (C18:1), 3 4-methylene heptanoylglycine, and sphingomyelin (d18: 2/18:1) are increased in a subject.

14. The method of claim 1, wherein the amounts of valerylcarnitine (C5), betaine, pyroglutamine, taurocyamine, phenol sulfate, dihomo-linolenoylcarnitine, and N-octanoylglycine are increased in a subject.

15. The method of claim 1, wherein the amounts of cytidine 5'-monophosphate (5'-CMP), 1-palmitoyl-2-linoleoyl-digalactosylglycerol (16:0/18:2), ursocholate, isovalerate, pipecolate, glucose, ethylmalonate, picolinate, 6-oxolithocholate, cysteine, 2-oxoarginine, N6-formyllysine, p-cresol sulfate, imidazole propionate, phenylacetylglycine, 1-palmitoleoylglycerol (16:1), cystathionine, palmitoleate (16:1n7), 4-hydroxyhippurate, 1-palmitoyl-2-oleoyl-GPI (16:0/18:1), and valylleucine are decreased in a subject.

16. The method of claim 1, wherein the biomarker is GABA/glutamate ratio.

17. The method of claim 1, wherein the biomarker is glutamine.

18. The method of claim 1, wherein the bacteria of the *Parabacteroides* (Pb) genus comprise *Parabacteroides merdae*.

19. The method of claim 1, wherein the bacteria of the *Parabacteroides* (Pb) genus comprise *Parabacteroides distasonis*.

20. The method of claim 18, wherein the bacteria of the *Akkermansia* (Akk) genus comprise *Akkermansia muciniphila*.

\* \* \* \* \*